US012630790B2

(12) United States Patent
Fan et al.

(10) Patent No.: US 12,630,790 B2
(45) Date of Patent: May 19, 2026

(54) SUBSTRATE, MICROFLUIDIC DEVICE, DRIVING METHOD AND MANUFACTURING METHOD

(71) Applicants: BEIJING BOE SENSOR TECHNOLOGY CO., LTD., Beijing (CN); BOE TECHNOLOGY GROUP CO., LTD., Beijing (CN)

(72) Inventors: Bolin Fan, Beijing (CN); Le Gu, Beijing (CN); Yingying Zhao, Beijing (CN); Wenliang Yao, Beijing (CN); Yongjia Gao, Beijing (CN); Qiuxu Wei, Beijing (CN)

(73) Assignees: Beijing BOE Sensor Technology Co., Ltd., Beijing (CN); BOE TECHNOLOGY GROUP CO., LTD, Beijing (CN)

( * ) Notice: Subject to any disclaimer, the term of this patent is extended or adjusted under 35 U.S.C. 154(b) by 1175 days.

(21) Appl. No.: 17/598,928

(22) PCT Filed: Dec. 25, 2020

(86) PCT No.: PCT/CN2020/139593
§ 371 (c)(1),
(2) Date: Sep. 28, 2021

(87) PCT Pub. No.: WO2022/134062
PCT Pub. Date: Jun. 30, 2022

(65) Prior Publication Data
US 2022/0403306 A1 Dec. 22, 2022

(51) Int. Cl.
*C12M 1/34* (2006.01)
*B01L 3/00* (2006.01)
(52) U.S. Cl.
CPC *C12M 1/34* (2013.01); *B01L 3/00* (2013.01)

(58) Field of Classification Search
CPC ....... G01N 1/38; B01L 3/502707; B01L 3/00; B01L 3/502792; B01L 2300/161;
(Continued)

(56) References Cited

U.S. PATENT DOCUMENTS 9,421,555 B2 * 8/2016 Lee ........................... B03C 1/02
9,782,775 B2 * 10/2017 Akella .................. F04B 19/006
(Continued)

FOREIGN PATENT DOCUMENTS

CN 1934443 A 3/2007
CN 103412023 A 11/2013
(Continued)

OTHER PUBLICATIONS

Extended European Search Report corresponding to European Application No. 20966626.2 (7 pages) (Jul. 5, 2023).
(Continued)

*Primary Examiner* — Shogo Sasaki
(74) *Attorney, Agent, or Firm* — Myers Bigel, P.A.

(57) ABSTRACT

Disclosed are a substrate for a microfluidic device, a microfluidic device, a driving method of the microfluidic device, and a method of manufacturing a substrate for the microfluidic device. The substrate includes: a first base substrate; a first electrode layer on the first base substrate, the first electrode layer including a plurality of drive electrodes. The plurality of drive electrodes define at least one flow channel and at least one functional area in the first substrate, the at least one functional area includes a reagent area, the at least one flow channel includes a reagent area flow channel, the reagent area includes a reagent area liquid storage portion and a droplet shape changing portion, the droplet shape changing portion is adjacent to the reagent area flow chan-
(Continued)

nel, and the reagent liquid storage portion is on a side of the droplet shape changing portion away from the reagent area flow channel.

21 Claims, 22 Drawing Sheets

(58) Field of Classification Search
CPC ....... B01L 2400/0427; B01L 2200/147; B01L 2200/16; B01L 2300/1827; B01L 2200/0605; C12M 1/34
See application file for complete search history.

(56) References Cited

U.S. PATENT DOCUMENTS

| | | | | |
|---|---|---|---|---|
| 11,517,902 | B2 * | 12/2022 | Walton | .............. B01L 3/502792 |
| 11,684,916 | B2 * | 6/2023 | Yao | .................. B01L 3/502792 |
| | | | | 422/502 |
| 2006/0020371 | A1 | 1/2006 | Ham et al. | |
| 2007/0242111 | A1 | 10/2007 | Pamula et al. | |
| 2008/0190219 | A1 | 8/2008 | Jensen et al. | |
| 2009/0304944 | A1 | 12/2009 | Sudarsan et al. | |
| 2010/0124791 | A1 | 5/2010 | Buckley et al. | |
| 2013/0092539 | A1 | 4/2013 | Pollack et al. | |
| 2020/0147612 | A1 | 5/2020 | Liu et al. | |
| 2020/0316606 | A1 | 10/2020 | Soto-Moreno et al. | |
| 2021/0060556 | A1 * | 3/2021 | Yao | ................... B01L 3/502715 |
| 2021/0197163 | A1 * | 7/2021 | Geng | ................ B01L 3/502792 |

FOREIGN PATENT DOCUMENTS

| | | | |
|---|---|---|---|
| CN | 205152235 | U | 4/2016 |
| CN | 106198964 | A | 12/2016 |
| CN | 107118955 | A | 9/2017 |
| CN | 108424843 | A | 8/2018 |
| CN | 109465041 | A | 3/2019 |
| CN | 109557150 | A | 4/2019 |
| CN | 110773247 | A | 2/2020 |
| CN | 111029261 | A | 4/2020 |
| CN | 111250184 | A | 6/2020 |
| CN | 111266139 | A | 6/2020 |
| CN | 111670253 | A | 9/2020 |
| EP | 2189787 | A1 | 5/2010 |
| EP | 3623462 | A1 | 3/2020 |
| JP | H02145452 | A | 6/1990 |
| WO | 2005099419 | A2 | 10/2005 |
| WO | 2019186205 | A1 | 10/2019 |
| WO | 2020142938 | A1 | 7/2020 |

OTHER PUBLICATIONS

First Office Action for corresponding CN application No. 202080003662.8 with machine translation, Apr. 28, 2023, 20 pages.

* cited by examiner

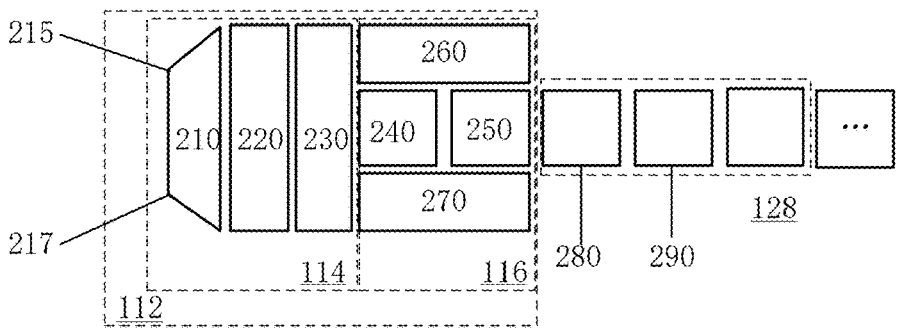
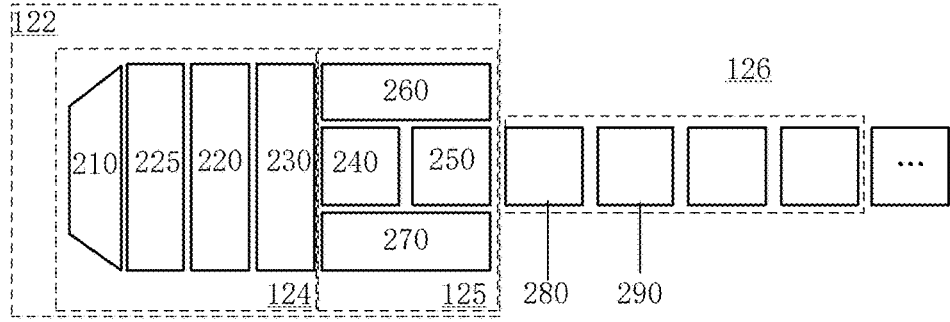
Fig.3c
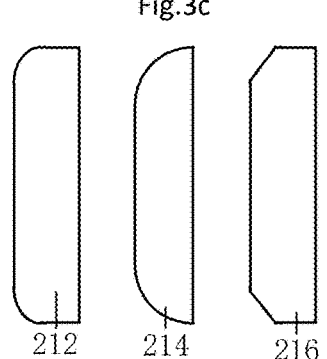
Fig.3d
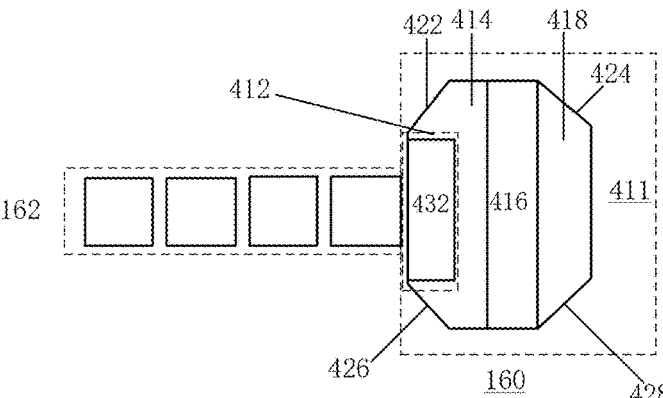
Fig.4

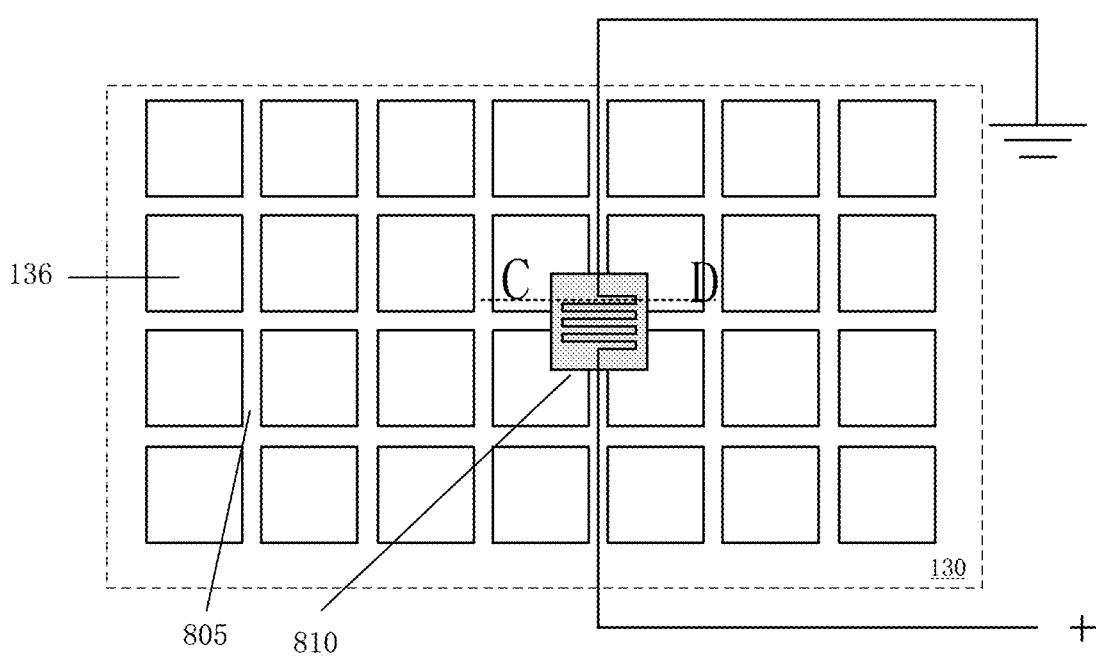
Fig.8a
Fig.8b
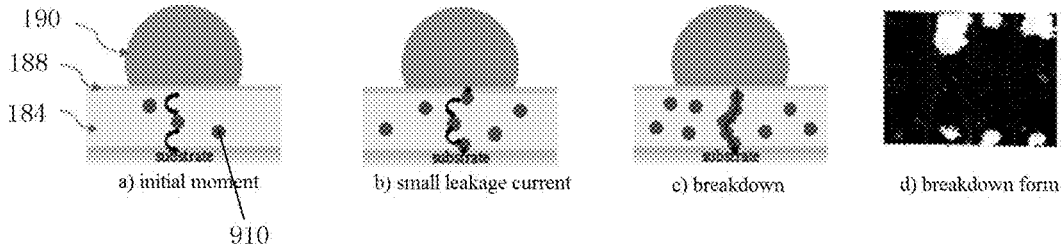
a) initial moment     b) small leakage current     c) breakdown     d) breakdown form
Fig.9

1020

1010 surface: temperature (degC) isoline:temperature (degC)

distance/mm   -15   0   15

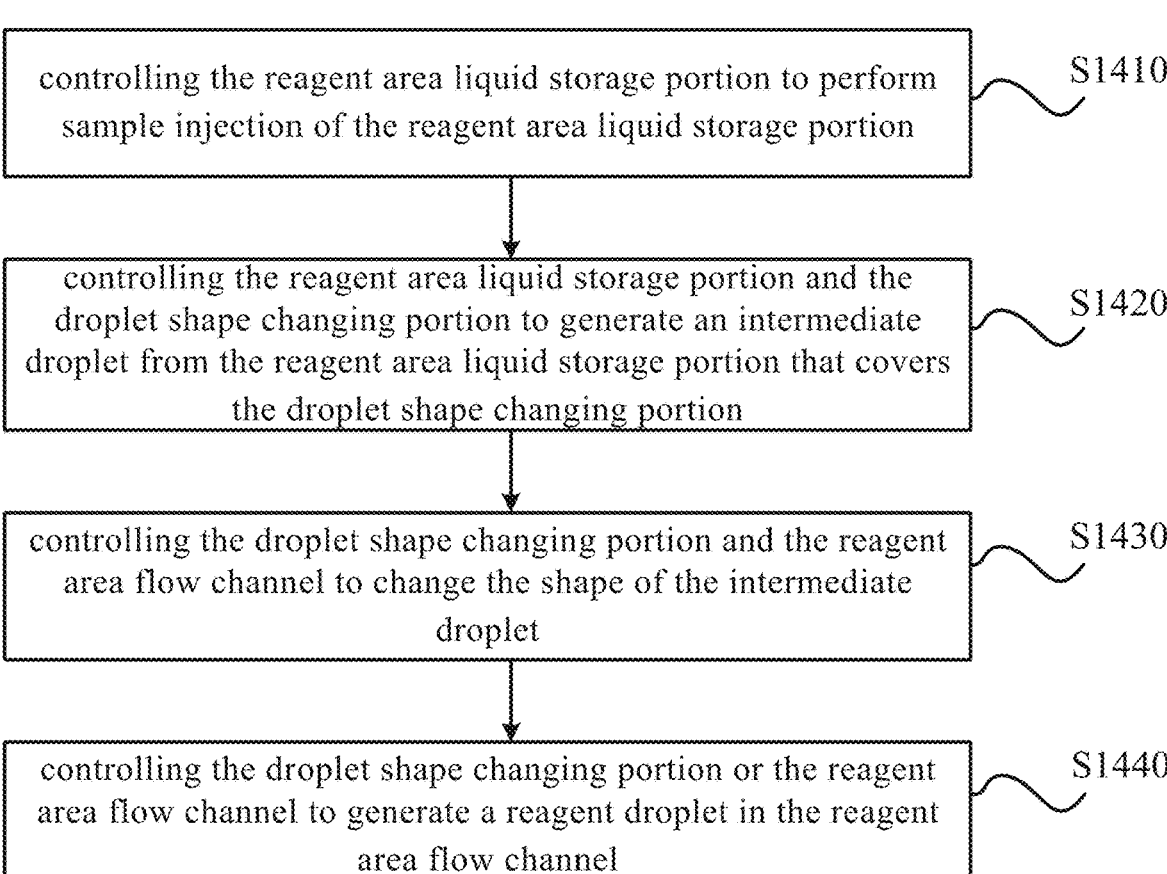

1400 controlling the reagent area liquid storage portion to perform sample injection of the reagent area liquid storage portion — S1410 controlling the reagent area liquid storage portion and the droplet shape changing portion to generate an intermediate droplet from the reagent area liquid storage portion that covers the droplet shape changing portion — S1420 controlling the droplet shape changing portion and the reagent area flow channel to change the shape of the intermediate droplet — S1430 controlling the droplet shape changing portion or the reagent area flow channel to generate a reagent droplet in the reagent area flow channel — S1440

Fig.14a

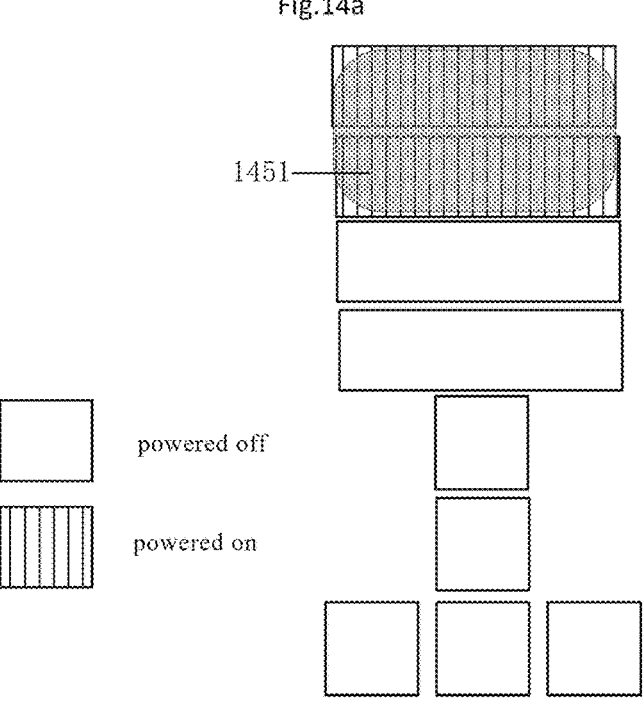

1451 powered off powered on

Fig.14b powered off powered on

1454

1455

1461 powered off powered on

344

354

364 366

374 376

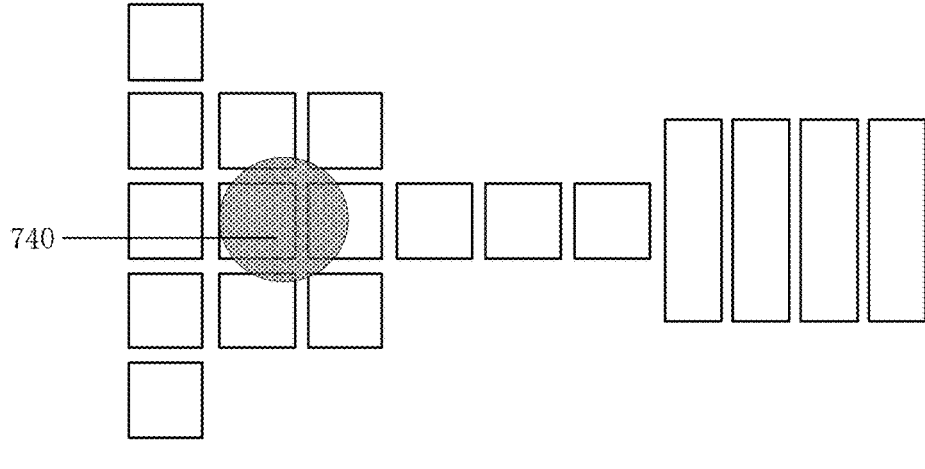

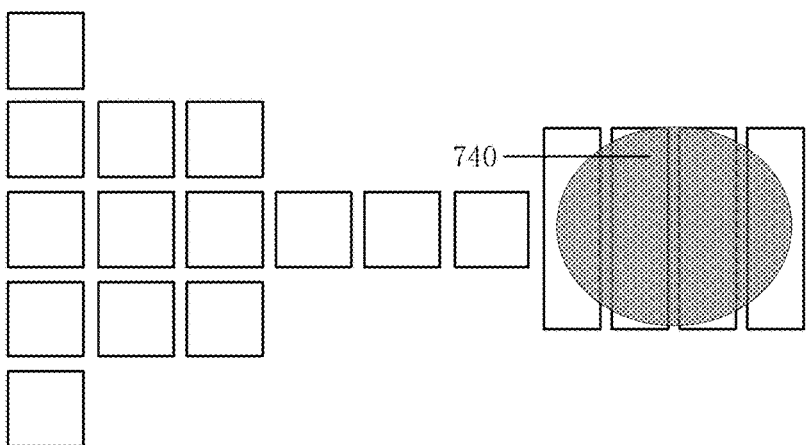

1900 preparing a first base substrate

S1910 preparing a first electrode layer on the base substrate, the first electrode layer including a plurality of drive electrodes, wherein the plurality of drive electrodes define at least one flow channel and at least one functional area in the first substrate, the at least one functional area includes a reagent area, the at least one flow channel includes a reagent area flow channel, the reagent area includes a reagent area liquid storage portion and a droplet shape changing portion, the droplet shape changing portion is adjacent to the reagent area flow channel, and the reagent area liquid storage portion is on a side of the droplet shape changing portion away from the reagent area flow channel, and wherein the reagent area liquid storage portion, the droplet shape changing portion, and the reagent area flow channel are configured to generate an intermediate droplet from the reagent area liquid storage portion that covers the droplet shape changing portion and configured to change the shape of the intermediate droplet to generate a reagent droplet in the reagent area flow channel

SUBSTRATE, MICROFLUIDIC DEVICE, DRIVING METHOD AND MANUFACTURING METHOD

RELATED APPLICATIONS

The present application is a 35 U.S.C. 371 national stage application of PCT International Application No. PCT/CN2020/139593 filed on Dec. 25, 2020, the entire disclosure of which is incorporated herein by reference.

TECHNICAL FIELD

The present disclosure relates to the field of biological detection, and more particularly to a substrate for a microfluidic device, a microfluidic device, a driving method of a microfluidic device, and a method of manufacturing a substrate for a microfluidic device.

BACKGROUND

A microfluidic device is also called Lab-on-a-chip, which refers to the integration of basic operation units, such as sample preparation, reaction, separation, and detection involved in the fields of biology, chemistry, and medicine, onto a chip with micrometer-scale microchannels, so that the whole process of reaction and analysis is automatically completed. The advantages of the analysis and detection device based on the microfluidic device may be, for example, a small amount of sample, a fast analysis speed, ease of making a portable instrument, and good suitability for real-time and on-site analysis. Moreover, the microfluidic device can be designed as a one-time use product, which can eliminate liquid path systems such as waste liquid treatment and complicated cleaning.

SUMMARY

In an aspect, embodiments of the present disclosure provide a first substrate for a microfluidic device, comprising: a first base substrate; a first electrode layer on the first base substrate, the first electrode layer comprising a plurality of drive electrodes; wherein the plurality of drive electrodes define at least one flow channel and at least one functional area in the first substrate, the at least one functional area comprises a reagent area, the at least one flow channel comprises a reagent area flow channel, the reagent area comprises a reagent area liquid storage portion and a droplet shape changing portion, the droplet shape changing portion is adjacent to the reagent area flow channel, and the reagent area liquid storage portion is on a side of the droplet shape changing portion away from the reagent area flow channel, and wherein the reagent area liquid storage portion, the droplet shape changing portion, and the reagent area flow channel are configured to generate an intermediate droplet from the reagent area liquid storage portion that covers the droplet shape changing portion and configured to change a shape of the intermediate droplet to generate a reagent droplet in the reagent area flow channel.

In some embodiments, the droplet shape changing portion comprises: a first electrode module comprising one or more electrodes, the first electrode module being arranged in a shape with a notch; and a second electrode module, the second electrode module being embedded in the notch, and wherein a sum of a projected area of the first electrode module on the first base substrate and a projected area of the second electrode module on the first base substrate is smaller than a projected area of the reagent area liquid storage portion on the first base substrate, and the reagent area flow channel comprises a drive electrode, and the second electrode module is adjacent to the drive electrode of the reagent area flow channel.

In some embodiments, the reagent area flow channel comprises a central axis, and the first electrode module is arranged in a symmetrical shape with respect to the central axis.

In some embodiments, an overall shape of a drive electrode comprised in the droplet shape changing portion is a rectangle with two sides perpendicular to an extending direction of the reagent area flow channel, and two corners of the rectangle on a side close to the reagent area flow channel are provided with chamfers.

In some embodiments, the first electrode module comprises a fourth electrode, a sixth electrode, and a seventh electrode, and the second electrode module comprises a fifth electrode, the reagent area liquid storage portion comprises a first electrode, a second electrode, and a third electrode sequentially arranged along an extending direction of the reagent area flow channel; the droplet shape changing portion comprises the fourth electrode and the fifth electrode sequentially arranged along the extension direction of the reagent area flow channel on a side of the third electrode away from the first electrode, and the sixth electrode and the seventh electrode on both sides of the fourth electrode and the fifth electrode perpendicular to the extension direction of the reagent area flow channel; and the reagent area flow channel comprises an eighth electrode and a ninth electrode sequentially arranged along the extending direction of the reagent area flow channel on a side of the fifth electrode away from the first electrode.

In some embodiments, the shape of the first electrode is a rectangle, two parallel sides of the rectangle are perpendicular to the extending direction of the reagent area flow channel, and the rectangle is provided with chamfers at two corners, and the two corners are away from the second electrode in a direction parallel to the extension direction of the reagent area flow channel.

In some embodiments, the at least one functional area further comprises a waste liquid area, and the at least one flow channel further comprises a waste liquid area flow channel, the waste liquid area comprises a waste liquid area liquid storage portion and a waste liquid area transition portion, the waste liquid area transition portion is adjacent to the waste liquid area flow channel, and the waste liquid area liquid storage portion is on a side of the waste liquid area transition portion away from the waste liquid area flow channel, a drive electrode comprised in the waste liquid area transition portion is in a long strip shape, long sides of the long strip shape are perpendicular to the extension direction of the waste liquid area flow channel, among drive electrodes comprised in the waste liquid area liquid storage portion a drive electrode adjacent to the waste liquid area transition portion comprises a notch, and the drive electrode comprised in the waste liquid area transition portion is embedded in the notch.

In some embodiments, the drive electrodes comprised in the waste liquid area are provided with chamfers at positions corresponding to corners of the waste liquid area.

In some embodiments, the at least one functional area further comprises a sample inlet area, and the at least one flow channel further comprises a sample inlet area flow channel, the sample inlet area comprises a sample inlet area liquid storage portion and a sample inlet area transition portion, the sample inlet area transition portion is adjacent to the sample inlet area flow channel, and the sample inlet area liquid storage portion is on a side of the sample inlet area transition portion away from the sample inlet area flow channel, among drive electrodes comprised in the sample inlet area liquid storage portion a drive electrode adjacent to the sample inlet area transition portion comprises a notch, and a drive electrode comprised in the sample inlet area transition portion is embedded in the notch.

In some embodiments, an overall shape of a drive electrode comprised in the sample inlet area is a rectangle with two sides perpendicular to an extending direction of the sample inlet area flow channel, and two corners of the rectangle on a side close to the sample inlet area flow channel are provided with chamfers.

In some embodiments, the at least one functional area further comprises a temperature control area, a sampling area and a quality detection area, and the at least one flow channel further comprises a temperature control area flow channel, a sampling area flow channel and a quality detection area flow channel.

In some embodiments, the first substrate has a rectangular shape, a direction parallel to two long sides of the rectangle is a first direction, and the first substrate comprises at least one column of temperature control branch, each column of the at least one column of temperature control branch extends along the first direction and comprises: the reagent area, the sampling area, the temperature control area, the sample inlet area and the waste liquid area sequentially arranged along the first direction.

In some embodiments, the first substrate further comprises: a first dielectric layer on a side of the first electrode layer away from the first base substrate.

In some embodiments, the first substrate further comprises: a first lyophobic layer on a side of the first dielectric layer away from the first base substrate.

In some embodiments, the temperature control area comprises an opening in the first electrode layer and between the drive electrodes, the temperature control area further comprises a temperature sensor, and the temperature sensor is provided in the opening.

In some embodiments, the material of the drive electrodes and the temperature sensor comprises molybdenum.

In some embodiments, the first substrate further comprises: coverings on the drive electrodes, wherein the coverings cover surfaces of the drive electrodes excluding a surface opposite to the first base substrate, and the material of the coverings comprises ITO.

In some embodiments, the first substrate further comprises: a covering on the temperature sensor, wherein the covering covers surfaces of the temperature sensor excluding a surface opposite to the first base substrate, and the material of the covering comprises ITO.

In some embodiments, the first substrate further comprises: a second electrode layer between the first base substrate and the first electrode layer; and an insulating layer between the first electrode layer and the second electrode layer, wherein, the second electrode layer comprises a plurality of leads, a drive electrode in the first electrode layer and a lead corresponding to the drive electrode are connected by a via hole, and the via hole penetrates the insulating layer.

In some embodiments, the first substrate further comprises: a second dielectric layer between the first dielectric layer and the first lyophobic layer.

In some embodiments, the second dielectric layer comprises a parylene layer.

In some embodiments, in one or more functional areas of the at least one functional area, the first lyophobic layer is patterned so that the second dielectric layer is periodically exposed.

In some embodiments, the material of the second dielectric layer comprises silicon oxide.

In some embodiments, the material of the first dielectric layer comprises aluminum oxide or polyimide.

In some embodiments, the first base substrate comprises glass.

According to another aspect, embodiments of the present disclosure further provide a microfluidic device, comprising any of the first substrates described above, and a second substrate assembled with the first substrate, the second substrate comprising: a second base substrate; a conductive layer on the second base substrate; and a second lyophobic layer on a side of the conductive layer away from the second base substrate, wherein, a space is defined between the first substrate and the second substrate.

In some embodiments, a ground electrode is provided on periphery of the first substrate, and the conductive layer of the second substrate is electrically connected to the ground electrode.

According to a further aspect, embodiments of the present disclosure further provide a driving method for a microfluidic device, the microfluidic device comprising any of the first substrates described above, and a second substrate assembled with the first substrate, the second substrate comprises: a second base substrate; a conductive layer on the second base substrate; and a second lyophobic layer on a side of the conductive layer away from the second base substrate, wherein, a space is defined between the first substrate and the second substrate, the driving method comprising: controlling the reagent area liquid storage portion to perform sample injection of the reagent area liquid storage portion; controlling the reagent area liquid storage portion and the droplet shape changing portion to generate an intermediate droplet from the reagent area liquid storage portion that covers the droplet shape changing portion; controlling the droplet shape changing portion and the reagent area flow channel to change the shape of the intermediate droplet; and controlling the droplet shape changing portion or the reagent area flow channel to generate a reagent droplet in the reagent area flow channel.

In some embodiments, the droplet shape changing portion comprises: a first electrode module comprising one or more electrodes, the first electrode module being arranged in a shape with a notch; and a second electrode module, the second electrode module being embedded in the notch, and wherein a sum of a projected area of the first electrode module on the first base substrate and a projected area of the second electrode module on the first base substrate is smaller than a projected area of the reagent area liquid storage portion on the first base substrate, and the reagent area flow channel comprises a drive electrode, and the second electrode module is adjacent to the drive electrode of the reagent area flow channel, wherein, controlling the droplet shape changing portion and the reagent area flow channel to change the shape of the intermediate droplet comprises: powering on the first electrode module, the second electrode module, and the drive electrode of the reagent area flow channel to change the shape of the intermediate droplet, controlling the droplet shape changing portion or the reagent area flow channel to generate a reagent droplet in the reagent area flow channel comprises: powering off the second electrode module to generate the reagent droplet in the reagent area flow channel.

In some embodiments, the reagent area liquid storage portion comprises a first electrode, a second electrode, and a third electrode sequentially arranged along an extending direction of the reagent area flow channel; the droplet shape changing portion comprises a fourth electrode and a fifth electrode sequentially arranged along the extension direction of the reagent area flow channel on a side of the third electrode away from the first electrode, and a sixth electrode and a seventh electrode on both sides of the fourth electrode and the fifth electrode perpendicular to the extension direction of the reagent area flow channel; and the reagent area flow channel comprises an eighth electrode and a ninth electrode sequentially arranged along the extending direction of the reagent area flow channel on a side of the fifth electrode away from the first electrode, wherein, controlling the reagent area liquid storage portion to perform sample injection of the reagent area liquid storage portion comprises: powering on the first electrode, the second electrode, and the third electrode to perform the sample injection of the reagent area liquid storage portion, controlling the reagent area liquid storage portion and the droplet shape changing portion to generate an intermediate droplet from the reagent area liquid storage portion that covers the droplet shape changing portion comprises: powering off the first electrode, the second electrode, and the third electrode, and powering on the fourth electrode, the sixth electrode, and the seventh electrode; powering on the second electrode and the third electrode; powering off the third electrode, and simultaneously powering on the fifth electrode, the sixth electrode, the seventh electrode, the first electrode, and the second electrode, to generate an intermediate droplet from the reagent area liquid storage portion that covers the fourth electrode, the fifth electrode, the sixth electrode, and the seventh electrode, controlling the droplet shape changing portion and the reagent area flow channel to change the shape of the intermediate droplet comprises: powering off the sixth electrode and the seventh electrode, and powering on the eighth electrode; and powering on the ninth electrode to change the shape of the intermediate droplet, and controlling the droplet shape changing portion or the reagent area flow channel to generate a reagent droplet in the reagent area flow channel comprises: powering off the fifth electrode to generate the reagent droplet in the reagent area flow channel.

According to a further aspect, embodiments of the present disclosure further provide a method of manufacturing a first substrate for a microfluidic device, comprising preparing a first base substrate; preparing a first electrode layer on the first base substrate, the first electrode layer comprising a plurality of drive electrodes; wherein the plurality of drive electrodes define at least one flow channel and at least one functional area in the first substrate, the at least one functional area comprises a reagent area, the at least one flow channel comprises a reagent area flow channel, the reagent area comprises a reagent area liquid storage portion and a droplet shape changing portion, the droplet shape changing portion is adjacent to the reagent area flow channel, and the reagent area liquid storage portion is on a side of the droplet shape changing portion away from the reagent area flow channel, and wherein the reagent area liquid storage portion, the droplet shape changing portion, and the reagent area flow channel are configured to generate an intermediate droplet from the reagent area liquid storage portion that covers the droplet shape changing portion and configured to change a shape of the intermediate droplet to generate a reagent droplet in the reagent area flow channel.

In some embodiments, the first substrate further comprises a first dielectric layer on a side of the first electrode layer away from the first base substrate, the method of manufacturing a first substrate for a microfluidic device further comprises: preparing the first dielectric layer by atomic layer deposition.

BRIEF DESCRIPTION OF THE DRAWINGS

In order to more clearly describe the technical solutions in the embodiments of the present disclosure, the drawings that need to be used in the description of the embodiments will be briefly introduced below. Obviously, the drawings in the following description are only some embodiments of the present disclosure.

FIGS. 3*a*-3*c* respectively show arrangement schematic diagrams of a plurality of drive electrodes included in a reagent area and a reagent area flow channel according to some embodiments of the present disclosure;

FIG. 3*d* schematically shows some alternative shapes of the first electrode according to some embodiments of the present disclosure;

FIG. 4 shows an arrangement schematic diagram of a plurality of drive electrodes included in a waste liquid area and a waste liquid area flow channel according to some embodiments of the present disclosure;

FIG. 8*a* shows an arrangement schematic diagram of a plurality of drive electrodes and a temperature sensor included in a temperature control area according to some embodiments of the present disclosure;

FIG. 8*b* shows a cross-sectional view of the first substrate according to some embodiments of the present disclosure, which is taken along the position shown by the line C-D in FIG. 8*a;*

FIG. 9 schematically shows a principle diagram of breakdown of a dielectric layer at high temperature;

FIG. 13a schematically shows the surface of the first substrate opposite to the second substrate of the microfluidic device according to some embodiments of the present disclosure;

FIG. 13b schematically shows a cross-sectional view of a microfluidic device according to some embodiments of the present disclosure, which is taken along the position shown by the line E-F in FIG. 13a;

FIG. 14a schematically shows a flowchart of a driving method according to some embodiments of the present disclosure;

FIGS. 14b-14m schematically show a driving process for the reagent area according to some embodiments of the present disclosure;

FIGS. 16a-16c schematically show a driving process for the sample inlet area according to some embodiments of the present disclosure;

FIGS. 17a-17c schematically show a driving process for the sampling area according to some embodiments of the present disclosure;

FIGS. 18a-18c schematically show a driving process for a quality detection area according to some embodiments of the present disclosure;

FIG. 19 schematically shows a flowchart of a method of manufacturing a first substrate for a microfluidic device according to some embodiments of the present disclosure;

DETAILED DESCRIPTION

In order to make the objectives, technical solutions, and advantages of the embodiments of the present disclosure more clear, the technical solutions of the embodiments of the present disclosure will be described in further detail below in conjunction with the accompanying drawings.

The inventors of the present application find that the performance of the microfluidic device is directly related to the generation, manipulation, and temperature control accuracy of the droplet by the microfluidic device, and the manufacturing process of the microfluidic device. Therefore, the following problems of the microfluidic device in some related art will affect the performance of the microfluidic device: (1) the generation and manipulation accuracy of the droplet need to be improved; (2) the temperature control accuracy of the droplet needs to be improved; (3) the movement speed of the droplet needs to be improved; and (4) the driving voltage needs to be reduced.

In view of at least some of the above problems, this application proposes a substrate for a microfluidic device, a microfluidic device, a driving method for a microfluidic device, and a method for manufacturing a substrate for a microfluidic device.

Figures 1, 2:
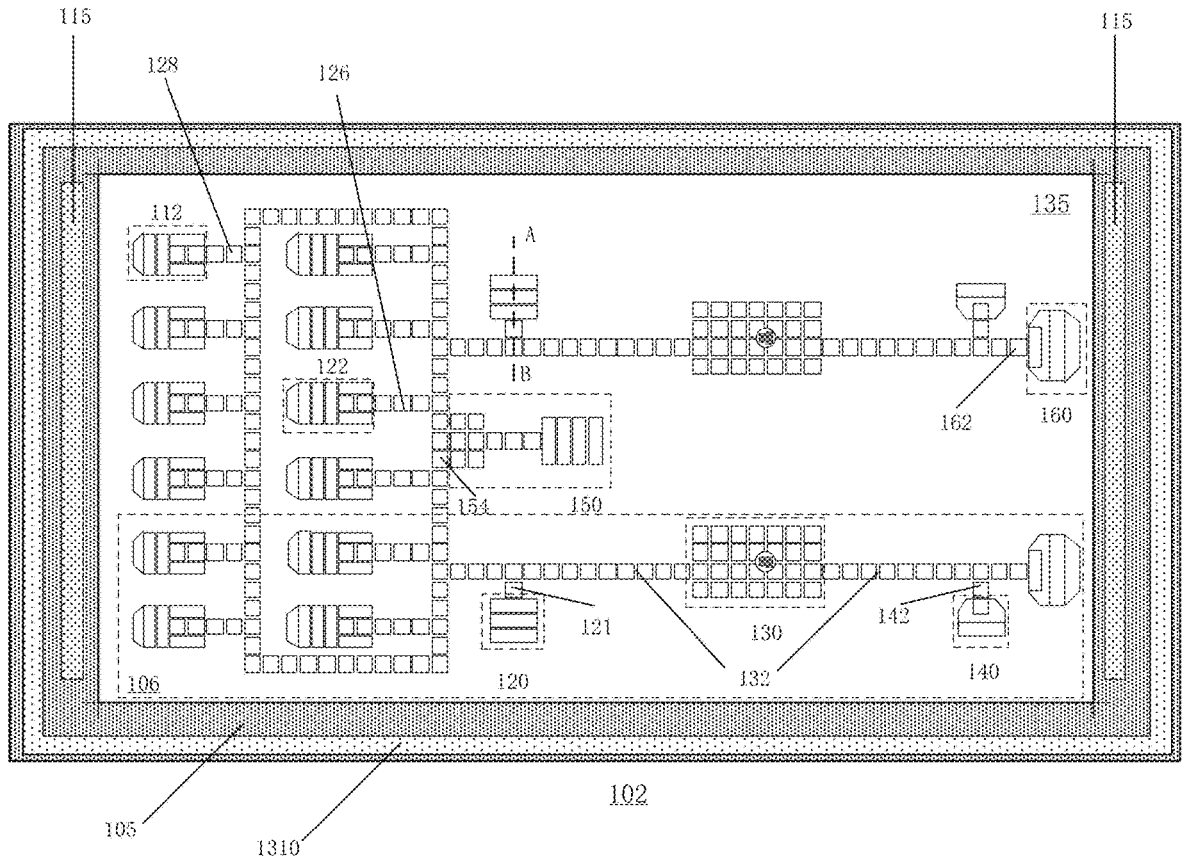
FIG. 1 shows a schematic top view of a first substrate of a microfluidic device according to some embodiments of the present disclosure.
FIG. 2 shows a cross-sectional view of the first substrate of the microfluidic device taken along the line A-B in FIG. 1.
Figures 3A, 3B:
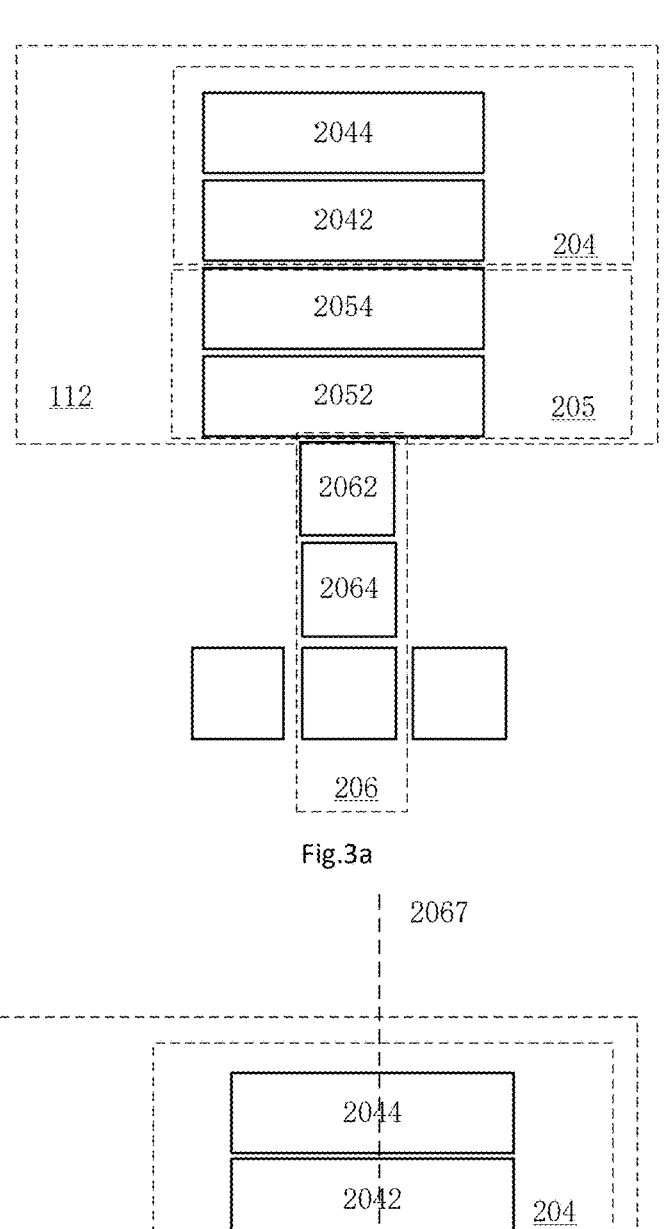

FIG. 1 shows a schematic top view of a first substrate 102 of a microfluidic device according to some embodiments of the present disclosure. FIG. 2 shows a cross-sectional view of the first substrate 102 of the microfluidic device taken along the line A-B in FIG. 1. FIG. 3a shows an arrangement schematic diagram of a plurality of drive electrodes 170 included in a reagent area and a reagent area flow channel according to some embodiments of the present disclosure. In some embodiments, as shown in FIG. 1, the first substrate 102 includes an operation area 135 and a peripheral area 105, and the peripheral area 105 may include a bonding area 115. In some embodiments, the peripheral area 105 may further include a ground electrode area 1310 (see the description of FIG. 13a below).

With reference to the FIGS. 1, 2 and 3a, in some embodiments, the first substrate 102 for the microfluidic device includes: a first base substrate 180; a first electrode layer 183 on the first base substrate, the first electrode layer including a plurality of drive electrodes 170. The plurality of drive electrodes 170 define at least one flow channel 128 (126), 121, 132, 142, 154, 162 and at least one functional area 112 (122), 120, 130, 140, 150, 160 in the first substrate (in particular, in the operation area 135), the at least one functional area 112 (122), 120, 130, 140, 150, 160 includes a reagent area 112 (122), the at least one flow channel 128 (126), 121, 132, 142, 154, 162 includes a reagent area flow channel 128 (126). The reagent area 112 includes a reagent area liquid storage portion 204 and a droplet shape changing portion 205. The droplet shape changing portion 205 is adjacent to the reagent area flow channel 206, and the reagent area liquid storage portion 204 is on a side of the droplet shape changing portion 205 away from the reagent area flow channel 206. The reagent area liquid storage portion 204, the droplet shape changing portion 205, and the reagent area flow channel 206 are configured to generate an intermediate droplet from the reagent area liquid storage portion 204 that covers the droplet shape changing portion 205 and configured to change a shape of the intermediate droplet to generate reagent droplet in the reagent area flow channel 206.

The material of the drive electrodes 170 may be a metal, an alloy, a conductive oxide, a composite film layer, or other conductive materials. In some embodiments, the material of the drive electrodes 170 includes molybdenum. In some embodiments, the thickness of the first electrode layer (i.e., the thickness of the drive electrodes 170) may be 220 nm.

In some embodiments, as shown in FIG. 1, the number of reagent areas can be two or more, to introduce different reagents into the microfluidic device respectively. For example, different reagent areas can have different sizes, which can be achieved by adjusting the shape or number of electrodes that define the reagent areas. For example, different reagent areas may be arranged in an array, for example, may be arranged in a three-row array, where the first row includes 9 reagent areas, and the second and third rows include 8 reagent areas respectively.

The reagent area liquid storage portion and the droplet shape changing portion are arranged in the reagent area defined by the drive electrodes, the droplet shape changing portion is adjacent to the reagent area flow channel, and the reagent area liquid storage portion is on a side of the droplet shape changing portion away from the reagent area flow channel, which avoids the solution that the reagent area liquid storage portion is directly adjacent to the reagent area flow channel. With this arrangement, the accuracy of droplet generation and manipulation in the reagent area will not decrease with the decrease of the reagent in the reagent area liquid storage portion. The drive electrodes are arranged to form three sections corresponding to the reagent area liquid storage portion, the droplet shape changing portion, and the reagent area flow channel, respectively. The reagent area liquid storage portion, the droplet shape changing portion, and the reagent area flow channel are configured to generate an intermediate droplet from the reagent area liquid storage portion that covers the droplet shape changing portion and configured to change a shape of the intermediate droplet to generate a reagent droplet in the reagent area flow channel. Through this three-section design, an intermediate droplet shape changing portion is introduced, which can cooperate with the reagent area liquid storage portion and the reagent area flow channel to generate the intermediate droplet in the process of generating the reagent droplet and to manipulate the shape of the intermediate droplet, which ensures the consistency of the volumes of intermediate droplets before final droplets are generated, thereby ensuring the consistency of the volumes of the finally generated reagent droplets.

Taking dielectric wetting driving as an example, after testing, when the volumes of the intermediate droplets are consistent before the droplet generation, the CV of 30 times of droplet generation can be controlled at about 1%, and stability and accuracy of droplet generation can be greatly improved.

For example, as shown in FIG. 3a, the reagent area liquid storage portion 204 may include drive electrodes 2044 and 2042 sequentially arranged along an extending direction of the reagent area flow channel 206; the droplet shape changing portion 205 may include drive electrodes 2054 and 2052 sequentially arranged along the extension direction of the reagent area flow channel 206 on a side of the drive electrode 2042 away from the drive electrode 2044; the reagent area flow channel 206 includes drive electrodes 2062, 2064 sequentially arranged along the extension direction of the reagent area flow channel 206 on a side of the drive electrode 2052 away from the drive electrode 2044. A sum of a projected areas of the drive electrodes 2054 and 2052 on the first base substrate 180 is smaller than a projected area of the reagent area liquid storage portion 204 on the first base substrate 180, to ensure that the consistency of the volumes of the intermediate droplets before the final droplet generation.

It should be understood that the present disclosure does not limit the types of reagents, as long as the reagents can be driven by the structure proposed in the present disclosure and can achieve the purpose of the present invention, such as water, organic solution, inorganic solution, biomolecule solution, conductive liquid, electrolyte solution or ionic liquid, etc.

It should be understood that in the description of the present disclosure, the term "flow channel" refers to some areas connecting at least one functional area of the first substrate, where the fluid driven by the microfluidic device in operation may flow through these areas. A "flow channel" does not necessarily mean that there is a channel physically lower than other planes.

In some embodiments, as shown in FIG. 3b, the droplet shape changing portion 205 may include: a first electrode module 2056 including one or more electrodes, the first electrode module 2056 being arranged in a shape with a notch; and a second electrode module 2058, the second electrode module 2058 being embedded in the notch, and a sum of a projected area of the first electrode module 2056 on the first base substrate 180 and a projected area of the second electrode module 2058 on the first base substrate 180 is smaller than a projection area of the reagent area liquid storage portion 204 on the first base substrate 180, and the reagent area flow channel 206 includes a drive electrode 2066, and the second electrode module 2058 is adjacent to the drive electrode 2066 of the reagent area flow channel 206.

When a reagent droplet is generated, an arc-shaped solitary area can be generated during the droplet generation process. Without the second electrode module 2058, the arc-shaped solitary area may cause the projected area of the reagent droplet on the first base substrate to be larger than a projected area of the drive electrode on the first base substrate when the reagent droplet is generated on the reagent area flow channel, resulting in inaccurate volume of the generated reagent droplet. The first electrode module 2056 is arranged in a shape with the notch, and the second electrode module 2058 is embedded in the notch to firstly generate an intermediate droplet, and the splitting and shape of the reagent droplet can be adjusted by controlling the second electrode module 2058 when the reagent droplet is generated, so that the arc-shaped solitary area exists inside the reagent area without affecting the projected area of the generated sample droplet, thereby improving the accuracy and stability of the droplet generation (referring to the description of the reagent area driving process in FIGS. 14b-14i).

In some embodiments, the reagent area flow channel 206 includes a central axis 2067, and the first electrode module 2056 is arranged in a symmetrical shape with respect to the central axis 2067. By arranging the first electrode module 2056 in a symmetrical shape with respect to the central axis 2067, the movement and deformation of the intermediate droplets can be accurately controlled when the reagent droplets are generated, avoiding loss of control or reduced control accuracy of droplet movement caused by the difference in the movement of the droplets on both sides of the central axis 2067.

In some embodiments, as shown in FIG. 3c, the reagent area 112 includes a reagent area liquid storage portion 114 and a droplet shape changing portion 116. The droplet shape changing portion 116 is adjacent to the reagent area flow channel 128, and the reagent area liquid storage portion 114 is on a side of the droplet shape changing portion 116 away from the reagent area flow channel 128. The reagent area liquid storage portion 114, the droplet shape changing portion 116, and the reagent area flow channel 128 are configured to generate an intermediate droplet from the reagent area liquid storage portion 114 that covers the droplet shape changing portion 116 and configured to change a shape of the intermediate droplet to generate a reagent droplet in the reagent area flow channel 128.

In some embodiments, as shown in FIG. 3c, the reagent area 122 includes a reagent area liquid storage portion 124 and a droplet shape changing portion 125. The droplet shape changing portion 125 is adjacent to the reagent area flow channel 126, and the reagent area liquid storage portion 124 is on a side of the droplet shape changing portion 125 away from the reagent area flow channel 126. The reagent area liquid storage portion 124, the droplet shape changing portion 125, and the reagent area flow channel 126 are configured to generate an intermediate droplet from the reagent area liquid storage portion 124 that covers the droplet shape changing portion 125 and configured to change a shape of the intermediate droplet to generate a reagent droplet in the reagent area flow channel 126.

In some embodiments, as shown in FIG. 3c, for the reagent area 112, the first electrode module 2056 includes a fourth electrode 240, a sixth electrode 260, and a seventh electrode 270, and the second electrode module 2058 includes a fifth electrode 250, the reagent area liquid storage portion 114 includes a first electrode 210, a second electrode 220, and a third electrode 230 sequentially arranged along an extending direction of the reagent area flow channel 128; the droplet shape changing portion 116 includes the fourth electrode 240 and the fifth electrode 250 sequentially arranged along the extension direction of the reagent area flow channel 128 on a side of the third electrode 230 away from the first electrode 210, and the sixth electrode 260 and the seventh electrode 270 on both sides of the fourth electrode 240 and the fifth electrode 250 perpendicular to the extension direction of the reagent area flow channel 128; and the reagent area flow channel 128 includes an eighth electrode 280 and a ninth electrode 290 sequentially arranged along the extending direction of the reagent area flow channel 128 on a side of the fifth electrode 250 away from the first electrode 210.

In some embodiments, as shown in FIG. 3c, for the reagent area 122, the drive electrodes included in the reagent area liquid storage portion 124, the droplet shape changing portion 125, and reagent area flow channel 126 are similar to the arrangement of the drive electrodes included in the reagent area liquid storage portion 114, the droplet shape changing portion 116 and the reagent area flow channel 128, with a difference that the reagent area liquid storage portion 124 additionally includes an additional electrode 225 between the first electrode 210 and the second electrode 220. With this arrangement, the liquid storage capacity of the reagent area liquid storage portion 124 is larger (for example, about ⅓ larger) than that of the reagent area liquid storage portion 114. For example, the reagent area 122 can be used for the generation of 1-3 μL droplets, and the reagent area 112 can be used for the generation of 1-2 μL droplets. Different reagent areas can be selected according to the specific reagent dosage.

Through the specific arrangement of the drive electrodes shown in FIG. 3c, some specific implementations of the reagent area liquid storage portion, the droplet shape changing portion, and the reagent area flow channel discussed above are provided. Through this specific arrangement of drive electrodes, an intermediate droplet covering the droplet shape changing portion is generated, and the drive electrodes can be configured to change a shape of the intermediate droplet to form an elongated droplet covering the fourth electrode 240, the fifth electrode 250, the eighth electrode 280 and the ninth electrode 290, ensuring the consistency of the volumes of the intermediate droplets before the final reagent droplets are generated. Furthermore, the elongated droplet is split to generate reagent droplets, which ensures the consistency of volumes of the finally generated reagent droplets, which can further improve the stability and accuracy of the reagent droplet generation (referring to description of the reagent area driving process in FIGS. 14j-14m).

In some embodiments, as shown in FIGS. 3c-3d, the shape of the first electrode 210 may be a rectangle, two parallel sides of the rectangle of the first electrode 210 are perpendicular to the extension direction of the reagent area flow channel 128, and the rectangle is provided with chamfers at the two corners 215, 217, and the two corners 215,

217 are away from the second electrode 220 in a direction parallel to the extension direction of the reagent area flow channel 128.

In some embodiments, some alternative shapes of the first electrode 210 are shown in FIG. 3d. It should be understood that the present disclosure does not limit the specific size of the chamfer. The chamfer may also include a beveling angle (an example of such a drive electrode is indicated by 216) or a round angle (an example of such a drive electrode is indicated by 212). In the case where the size of the chamfer is sufficiently large, the first electrode 210 may be formed in a trapezoidal shape (an example of such a drive electrode is indicated by 210) or a shape with two sides in an arc shape (an example of such a drive electrode is indicated by 214).

Through the chamfer design, the dead volume in the droplet generation process can be reduced, and the liquid storage accuracy of the reagent area liquid storage portion can be improved. The "dead volume" here refers to the uncontrollable volume during the reagent injection process. Specifically, if the first electrode 210 adopts a rectangular electrode, its electric field is distributed in a rectangle. Due to the presence of the surface tension of the droplet, the position of the droplet at the edge of the rectangular electrode is not at right angles (that is, it cannot perfectly match the shape of the rectangular electrode). The shape and volume of the droplet will change, and there is certain randomness in this change of shape and volume, which introduces a dead volume. This may cause different reagent areas or the same reagent area in different operations of the microfluidic device to have different liquid storage volumes in the reagent area liquid storage portion, which in turn leads to a decrease in the accuracy of droplet manipulation. When the chamfer design is adopted, the electric field distribution also changes with the design of the electrode shape, which can make the shape matching between the droplet and the electrode better, thereby effectively reducing the difference in liquid storage volume and improving the accuracy of droplet manipulation.

In some embodiments, in the embodiment shown in FIG. 3b, overall shapes of drive electrodes 2054, 2052 (or 2056, 2058) included in the droplet shape changing portion 205 are rectangles having two sides perpendicular to the extending direction of the reagent area flow channel 206. The rectangles are provided with chamfers at two corners 2046, 2018 on a side close to the reagent area flow channel. The specific manner of setting each chamfer can be similar to that of the first electrode 210, and will not be repeated here. The electric field formed by using the chamfered electrode here has a better matching with the actual shape of the droplet in each stage in the reagent droplet generation process (which may refer to description of the reagent area driving process in FIGS. 14b-14i). The electrode control accuracy can be improved, thereby improving the accuracy and stability of droplet generation.

For example, in FIG. 3c, the shape of the first electrode 210 is an isosceles trapezoid with an upper side of 1 mm, a lower side of 3 mm, and a height of 1 mm. The shapes of the second electrode 220, the additional electrode 225, and the third electrode 230 are rectangles of 1 mm*3 mm, the shape of the sixth electrode 260 and the seventh electrode 270 are rectangles of 1 mm*2 mm, the shape of the fourth electrode 240 and the fifth electrode 250 are squares of 1 mm*1 mm, and the shape of the eighth electrode 280 and the ninth electrode 290 are 1 mm*1 mm square electrodes. For example, the spacing between the drive electrodes is 100 μm.

FIG. 4 shows an arrangement schematic diagram of a plurality of drive electrodes 170 included in a waste liquid area and a waste liquid area flow channel according to some embodiments of the present disclosure. In some embodiments, referring to FIGS. 1 and 4, the at least one functional area 112 (122), 120, 130, 140, 150, 160 further includes a waste liquid area 160, and the at least one flow channel 128 (126), 121, 132, 142, 154, 162 includes a waste liquid area flow channel 162. The waste liquid area 160 includes a waste liquid area liquid storage portion 411 and a waste liquid area transition portion 412. The waste liquid area transition portion 412 is adjacent to the waste liquid area flow channel 162, and the waste liquid area liquid storage portion 411 is on a side of the waste liquid area transition portion 412 away from the waste liquid area flow channel 162. A drive electrode 432 included in the waste liquid area transition portion 412 is in a long strip shape, long sides of the long strip shape are perpendicular to the extending direction of the waste liquid area flow channel 162. Among drive electrodes 414, 416, 418 included in the waste liquid area liquid storage portion 411 a drive electrode adjacent to the waste liquid area transition portion 412 includes a notch, and the drive electrode included in the waste liquid area transition portion 412 is embedded in the notch. By introducing the drive electrode 432 included in the waste liquid area transition portion 412, the stability and accuracy of the droplet driving can be improved. The reason is as follow: if the waste liquid area transition portion 412 adjacent to the waste liquid area flow channel 162 is not used, the size of the drive electrode adjacent to the waste liquid area flow channel 162 among the electrodes of the waste liquid area liquid storage portion 411 is too large, its uniform-intensity electric field has a relatively large range, and the randomness of the position of the droplet after moving to this drive electrode increases, which may affect the stability and accuracy of the droplet driving.

In some embodiments, the drive electrodes included in the waste liquid area 160 are provided with chamfers at positions 422, 424, 426, 428 corresponding to the corners of the waste liquid area 160. The specific manner of setting each chamfer can be similar to that for the first electrode 210, and will not be repeated here. The waste liquid can be taken out of the waste liquid area 160 with a pipette gun or a plastic dropper. Since the volume of the waste liquid in the waste liquid area 160 can be relatively large (>30 μL) and the size of the pipette gun or plastic dropper is fixed, the use of chamfer design can reduce the dead volume in the process of droplet manipulation and prevent the occurrence of liquid extraction residues in the process of waste liquid extraction.

For example, the waste liquid area 160 includes an isosceles trapezoidal electrode 418 with an upper side of 4 mm, a lower side of 5 mm, and a height of 1 mm; a rectangular electrode 416 of 1 mm*5 mm; an electrode 414 including a notch with a height of 2 mm, being capable of embedding a rectangular shape of 1 mm*3 mm, a long side of 5 mm, two short sides of 0.5 mm perpendicular to the long side, and a trapezoidal transition of 1 mm; and a rectangular electrode 432 of 1 mm*3 mm. For example, the spacing between the drive electrodes is 100 μm.

In some embodiments, when the waste liquid is generated, the waste liquid droplets move from other areas to the waste liquid area, and finally gather in the waste liquid area liquid storage portion 411. For example, the volume of the waste liquid droplet is 1-3 μL.

Figure 5:
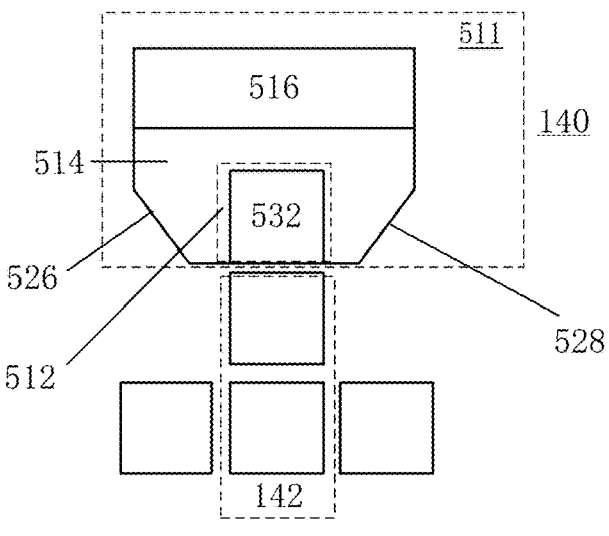
FIG. 5 shows an arrangement schematic diagram of a plurality of drive electrodes included in a sample inlet area and a sample inlet area flow channel according to some embodiments of the present disclosure.

FIG. 5 shows an arrangement schematic diagram of a plurality of drive electrodes 170 included in a sample inlet area and a sample inlet area flow channel according to some embodiments of the present disclosure. In some embodiments, referring to FIGS. 1 and 5, at least one functional area 112 (122), 120, 130, 140, 150, 160 further includes a sample inlet area 140, and at least one flow channel 128 (126), 121, 132, 142, 154, and 162 includes a sample inlet area flow channel 142. The sample inlet area 140 includes a sample inlet area liquid storage portion 511 and a sample inlet area transition portion 512. The sample inlet area transition portion 512 is adjacent to the sample inlet area flow channel 142, and the sample inlet area liquid storage portion 511 is on a side of the sample inlet area transition portion 512 away from the sample inlet area flow channel 142. For the drive electrodes 514 and 516 included in the sample inlet area liquid storage portion 511, the drive electrode adjacent to the sample inlet area transition portion 512 includes a notch, and the drive electrode 532 included in the sample inlet area transition portion 512 is embedded in the notch. When a droplet with a very small volume (for example, 1 μL) is generated, without setting the sample inlet area transition portion 512, an arc-shaped solitary area will be generated during the droplet generation process. When the sample droplet is being generated, the arc-shaped solitary area exists on the sample inlet area flow channel, which may cause the projected area of the generated sample droplet on the first base substrate to be larger than the projected area of the drive electrode on the first base substrate, making the volume of the sample droplet inaccurate. The drive electrode included in the sample inlet area liquid storage portion 511 adopts a design including a notch. When a droplet is being generated, the drive electrode included in the sample inlet area transition portion 512 can be controlled to adjust the splitting and shape of the droplet, so that the existence of the arc-shaped solitary area inside the sample inlet area will not affect the projected area of the generated sample droplets, thereby improving the accuracy and stability of droplet generation (referring to the description of the sample inlet area driving process in FIGS. 16a-16c).

In some embodiments, an overall shape of the drive electrodes 532, 514, and 516 included in the sample inlet area 140 is a rectangle with two sides perpendicular to the extension direction of the sample inlet area flow channel 142, and two corners 526 and 528 of the rectangle on a side close to the sample inlet area flow channel 142 are provided with chamfers. The specific manner of setting each chamfer can be similar to that for the first electrode 210, and will not be repeated here. The electric field formed by using the chamfered electrode here has a higher match with the actual shape of the droplet in each stage of the droplet generation process in the sample inlet area (referring to the description of the sample inlet area driving process in FIGS. 16a-16c), which can improve the accuracy of electrode control, thereby improving the accuracy and stability of droplet generation.

For example, as shown in FIG. 5, the sample inlet area 140 includes a 1 mm*3 mm rectangular electrode 516, a notched electrode 514 (with a height of 2 mm, a long side of 3 mm, and two short sides of 0.5 mm perpendicular to the long side, and a trapezoidal transition of 1 mm) which can embed a rectangle of 1 mm*1.2 mm, and a 1 mm*1 mm square electrode 532.

Figure 6:
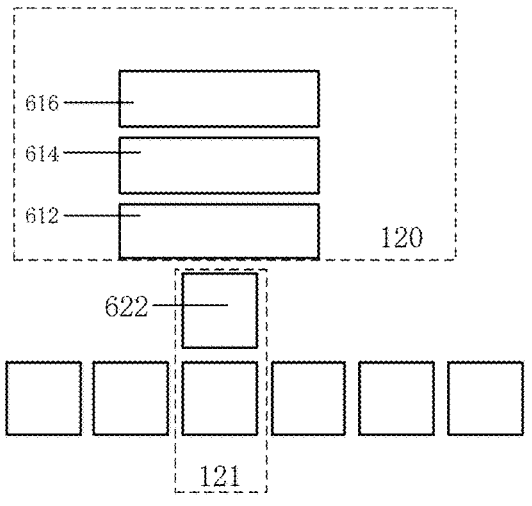
FIG. 6 shows an arrangement schematic diagram of a plurality of drive electrodes included in a sampling area and a sampling area flow channel according to some embodiments of the present disclosure.
Figure 7:
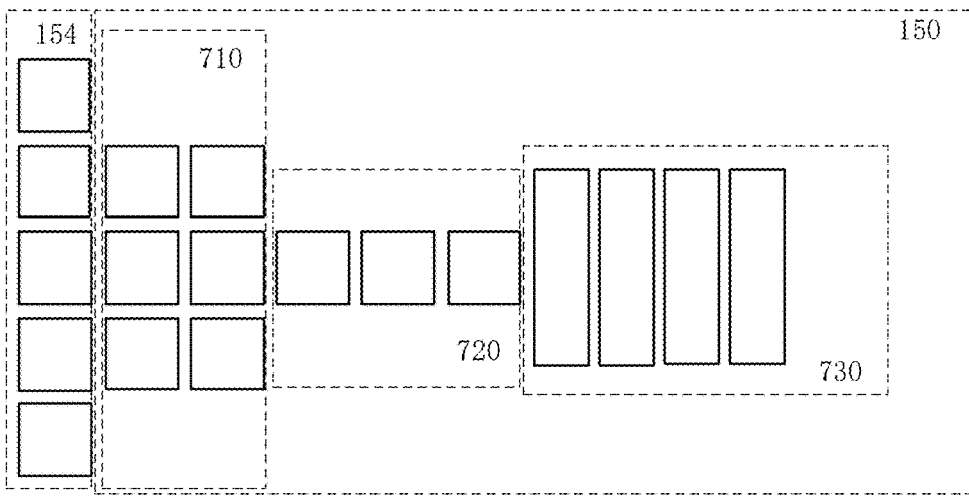
FIG. 7 shows an arrangement schematic diagram of a plurality of drive electrodes included in a quality detection area and a quality detection area flow channel according to some embodiments of the present disclosure.

FIG. 6 shows an arrangement schematic diagram of a plurality of drive electrodes 170 included in a sampling area and a sampling area flow channel according to some embodiments of the present disclosure. FIG. 7 shows an arrangement schematic diagram of a plurality of drive electrodes 170 included in a quality detection area and a quality detection area flow channel according to some embodiments of the present disclosure. FIG. 8*a* shows an arrangement schematic diagram of a plurality of drive electrodes 170 and a temperature sensor included in a temperature control area 130 according to some embodiments of the present disclosure. In some embodiments, referring to FIGS. 1 and 6-8*a*, at least one functional area 112 (122), 120, 130, 140, 150, 160 further includes a sampling area 120, a quality detection area 150, and a temperature control area 130, at least one flow channel 128 (126), 121, 132, 142, 154, 162 further includes a sampling area flow channel 121, a quality detection area flow channel 154, and a temperature control area flow channel 132.

In some embodiments, as shown in FIG. 6, the sampling area 120 includes three rectangular electrodes 612, 614, and 616 of 1 mm*3 mm, and the sampling area flow channel 121 includes a square electrode 622 of 1 mm*1 mm.

In some embodiments, the sampling area 120 corresponds to the sampling port of the first substrate 102, and the center of a circle of the sampling port coincides with the center of the overall three 1 mm*3 mm rectangular electrodes 612, 614, and 616, so that sampling can be achieved from the sampling port through a plastic dropper or pipette. In some embodiments, a diameter of the sampling port is 2 mm.

In some embodiments, as shown in FIG. 7, the quality detection area 150 includes an detection area 710 (for example, an optical detection area), a flow channel 720 in the quality detection area, and a quality detection area waste liquid portion 730. For example, the drive electrodes included in the quality detection area 150 may include a plurality of square electrodes with a size of 1 mm*1 mm and a plurality of rectangular electrodes with a size of 1 mm*3 mm. The quality detection area 150 can realize the quality detection of the samples in the microfluidic device. For example, the droplets will move from other functional areas to the quality detection area 150 through the quality detection area flow channel 154. After the detection (such as optical detection) is completed in the detection area 710, the droplets move through the flow channel 720 in the quality detection area to the quality detection area waste liquid portion 730. In some embodiments, the quality detection sample can be taken out of the microfluidic device through the quality detection area waste liquid portion 730.

In some embodiments, as shown in FIG. 8*a*, the temperature control area 130 may include 1 mm*1 mm square electrodes 136 (4*7 in the figure) distributed in an array. In some embodiments, the temperature control area 130 may be heated to a relatively high temperature and maintained for a certain period of time, to provide conditions and places for operations such as reaction and mixing of the fluid in the microfluidic device.

Library preparation usually refers to the following process: constructing a nucleic acid sample that requires specific sequence information into a standardized nucleic acid library that can be sequenced for sequencing through a series of biomolecular techniques such as fragment interruption, repair, connection, and amplification. Library preparation is an important step in the gene sequencing process. One of its purposes is to increase the concentration of nucleic acid to be detected and prepare for subsequent sequencing work. The library preparation technology based on the microfluidic device can greatly reduce the library preparation time, reduce the amount of reagents used, and greatly improve the level of automation. Through the microfluidic device method, the library preparation time can be reduced from 2 days in the ordinary method to about 8 hours, which greatly shortens the library preparation time.

Taking the library preparation as an example, the role of at least one functional region is further illustrated below. With reference to FIGS. 1-8*a*, in the library preparation, the process of generating and manipulating droplets can include the following process. (1) Various reagents required for library preparation can be stored in each reagent area 112, 122 respectively, and when it is needed to extract the droplets of the reagent, the droplets of the reagent are generated and manipulated to move through the reagent area liquid storage portion, the droplet shape changing portion and the reagent area flow channel. (2) During the library construction process, the DNA samples whose library is needed to be constructed can be introduced into the microfluidic device from the sample inlet area 140, the amount of DNA sample used can be relatively low (for example, 1 μL), so a small volume of droplets (for example, 1 μL of droplets) needs to be generated at the sample inlet area 140. (3) The temperature control area 130 provides conditions and places for the mixing and reaction, etc. of different reagents and samples. (4) When waste liquid is generated, droplets (for example, the volumes of the droplets are 1-3 μL) can move from the temperature control area 130 to the waste liquid area 160, and finally gather in the waste liquid area liquid storage portion 411. (5) When the construction of the library is completed, the droplets (for example, the volumes of the droplets are 1-3 μL) move from the temperature control area 130 to the sampling area 120, and finally gather at the rectangular electrodes 612, 614, 616, so that sampling can be achieved from the sampling port with a plastic dropper or pipette. (6) During the entire library preparation process, the quality detections will be performed for about 2-5 times (for example, the volume of the droplet in each quality detection is 1-3 μL), the droplet will move from other functional areas to the quality detection area 150, and moves to the quality detection area waste liquid portion 730 (from which the droplet can be taken out of the microfluidic device) after the quality detection is completed in the detection area 710.

In some embodiments, the connection between the respective flow channels as shown in FIG. 1 may include square electrodes arranged at intervals (for example, the size is 1 mm*1 mm, and the interval is 100 μm). It should be understood that, within the scope of the present disclosure, different functional areas are not all necessary, and the positional relationship, size, and number of each functional area can be adjusted and set according to actual application requirements.

In some embodiments, as shown in FIG. 1, the first substrate has a rectangular shape, and the direction parallel to the two long sides of the rectangle is the first direction. The first substrate 102 includes at least one column of temperature control branch 106, and each column of the at least one column of temperature control branch extends along the first direction and includes: a reagent area 112 (122), a sampling area 120, a temperature control area 130, a sample inlet area 140, and a waste liquid area 160 sequentially arranged along the first direction. For example, FIG. 1 shows two temperature control branches. Such an arrangement can reduce cross-contamination between fluids, reduce the stroke of fluid movement, and improve the efficiency of detection.

In some embodiments, as shown in FIG. 1, various flow channels are arranged in a network, so that at least one functional area 112 (122), 120, 130, 140, 150, and 160 of the first substrate 102 can be in communication with each other through the flow channels, which allows the fluid droplets to move between the various functional areas of the microfluidic device as required, so that various manipulations, such as reaction, mixing, liquid separation, detection, etc., can be performed.

In some embodiments, as shown in FIG. 1, the quality detection area 150 is set near the middle position of the operation area 135 of the first substrate 102, so that it is convenient for the fluid in each functional area to enter the quality detection area 150 at a relatively short distance.

In some embodiments, at least one sampling area 112 may also be connected to the quality detection area 150 through a straight flow channel (not shown), so that the reagent in the reagent area can be directly detected without contaminating other flow channels. In some embodiments, the temperature control areas 130 located in adjacent temperature control branches can also be connected by a straight flow channel (not shown), which facilitates the fluid transfer between adjacent temperature control areas at a relatively short distance, such as rapid transfer to reaction conditions of different temperatures. It should be understood that "connected by a straight flow channel" means that the drive electrodes included in the flow channel between the two functional areas are arranged in a straight line.

It should be understood that the present disclosure does not limit the driving principle of the microfluidic device, as long as the structure proposed in the present disclosure can be used to drive and achieve the purpose of the present invention. The device that realizes microfluidic control based on drive electrodes includes various types of devices, e.g., devices based on the capillary phenomenon caused by the temperature difference, based on the wetting angle change on the medium of the double-layer substrate, based on the wetting angle change on the medium of the single-layer substrate, based on electrochemistry, etc. Hereinafter, some embodiments of the present disclosure will be described by taking the driving principle based on the wetting angle change on the medium of double-layer substrate as an example.

In some embodiments, the basic principle of the microfluidic device is the principle of dielectric wetting, and the basic formula of the principle of dielectric wetting is expressed as follows:

$$\cos\theta = \cos\theta_0 + \frac{\varepsilon_0\varepsilon_r\Delta V^2}{2d\gamma_{lg}} \qquad \text{Formula (1)}$$

where $\varepsilon_0$ is the dielectric constant, $\varepsilon_r$ is the relative dielectric constant of the dielectric layer, $\gamma_{lg}$ is the surface tension coefficient of the liquid-gas interface (when the droplet moves in the gas), $\Delta V$ is the potential difference between the two sides of the dielectric layer, and d is the thickness of the medium layer, $\theta_0$ is the initial contact angle of the droplet when no voltage is applied to the drive electrode, and $\theta$ is the contact angle of the droplet when the voltage is applied to the drive electrode.

In some embodiments, referring to FIG. 2, the first substrate 102 further includes: a first dielectric layer 184 on a side of the first electrode layer 183 away from the first base substrate 180. It should be understood that, as shown in FIG. 2, the first dielectric layer 184 may also exist in the gap between the drive electrodes 170. With reference to formula (1), the first dielectric layer 184 may serve as the dielectric layer in the formula, thereby providing the dielectric properties required to drive the change in the contact angle of the droplet. Starting from the principle of dielectric wetting, reducing the thickness of the first dielectric layer 184 and increasing the driving voltage can enhance the dielectric wetting effect. However, from the perspective of practical applications, too high driving voltage is not conducive to the miniaturization and integration of the microfluidic device, and a higher voltage will cause the irreversible breakdown of the first dielectric layer 184 and cause the failure of the microfluidic device. In addition, high voltage is prone to generate excessive heat and consumes a lot of power, therefore reducing the driving voltage is one of the important development directions of microfluidic devices. In this case, the first dielectric layer 184 (especially the thickness and dielectric properties) has an important influence on the performance of the microfluidic device.

In some embodiments, when working in a normal-temperature environment, the material of the first dielectric layer 184 can be highly selective, such as SiNx, non-metal oxides (such as silicon oxide), organic materials (such as Resin, SU8, polyimide film), and so on.

In some embodiments, in the biochemical reaction or detection, high temperature is one of the unavoidable environments for the application of the microfluidic device. For example, the reaction temperature of part of the process in the library preparation process is 65° C. and 95° C. The inventors of the present application find that bubbles are prone to appear on the surface of the organic layer during the preparation of the microfluidic device, and the compactness of this type of material is poor, and the material will absorb moisture in the environment after being placed for a long time, and its high-temperature resistance to breakdown is poor. After actual testing, the breakdown voltage of 1.5 μm-thick Resin material is 10 Vrms at 95° C. environment, while the saturation voltage of deionized water on this layer is about 60 Vrms, so this type of fluid cannot be driven. In addition, the breakdown of the 220 nm-thick SiNx layer at a voltage of 10 Vrms at 95° C. environment is also less than the saturation voltage of deionized water. FIG. 9 schematically shows a principle diagram of breakdown of a dielectric layer at high temperature. As shown in FIG. 9, the droplet 190 is located on the first lyophobic layer 188 (for the relevant arrangement of the droplet and the first lyophobic layer, please refer to the description below). Some metal oxide layers prepared by semiconductor processes are prepared by PECVD and other processes, and there are many pinholes 910. Due to the presence of defects such as pinhole, when the microfluidic device is working at high-temperature conditions, the ion activity increases as the temperature rises, and the number of pinholes 910 in the first dielectric layer 184 (and the optional second dielectric layer, for the related settings of the second dielectric layer please refer to the description below) is increased to form a conduction channel from the liquid drop to the drive electrode, a small leakage current will be generated and the leakage current will gradually increase, thereby generating a large leakage current and thermal breakdown.

In some embodiments, the material of the first dielectric layer includes aluminum oxide or polyimide. The relative dielectric constant of aluminum oxide or polyimide is relatively large.

In some embodiments, strict pre-treatment is performed before the preparation of the aluminum oxide layer to reduce the introduction of particles as much as possible, and the preparation of the aluminum oxide layer can be achieved by atomic layer deposition technology, which greatly reduces the defects of the dielectric layer This can achieve better high-temperature stability, enhance the breakdown resistance of the dielectric layer, and avoid irreversible dielectric breakdown at relatively low voltages.

In some embodiments, the polyimide layer can also be used to achieve stable driving of high-temperature droplets. The relative dielectric constant of the polyimide layer can be e.g., about 3.2, and the thickness can be e.g., 38 μm. The compactness of the polyimide layer can be increased by increasing the thickness of the layer, thereby preventing breakdown of the dielectric layer at high temperatures. In some cases, the method of increasing the thickness of the dielectric layer will lead to an increase in the driving voltage of the droplets. For example, the driving voltage of the droplets in the polyimide layer may be 180 Vrms.

In some embodiments, after testing, a microfluidic device made of such a first substrate 102 (the material of the first dielectric layer includes aluminum oxide or polyimide) can achieve a stable drive for 3 hours at a high temperature of 95° C., and when the aluminum oxide layer is used for the first dielectric layer, its driving voltage can be controlled at 20 Vrms, that is, the driving voltage can be reduced.

In some embodiments, referring to FIG. 2, the first substrate 102 further includes: a first lyophobic layer 188 on a side of the first dielectric layer 184 away from the first base substrate 180. The first lyophobic layer 188 can provide good contact performance with the droplets (for example, a suitable contact angle), and increase the controllability of the droplets. For example, the first lyophobic layer 188 can be made of materials such as Teflon or CYTOP. In this case, the contact angle of deionized water is no less than 110°, and the rolling inclination angle is less than or equal to 15°.

In some embodiments, the first substrate 102 further includes a temperature sensor. The temperature sensor is used to sense the temperature at certain positions of the first substrate, for example, to sense the temperature of certain functional areas, to facilitate the adjustment of the temperatures of the functional areas so that the functional areas meet the operating conditions of the reagent. In some embodiments, the temperature sensor adopts an external solution, that is, it is arranged near the first base substrate 180.

FIG. 8b shows a cross-sectional view of the first substrate 102, which is taken along the position shown by the line C-D in FIG. 8a. In some embodiments, referring to FIGS. 8a-8b, the first electrode layer 183 includes an opening 805 between the drive electrodes 170, the first substrate 102 further includes a temperature sensor 810, and the temperature sensor 810 is provided in the opening 805. In some embodiments, referring to FIGS. 8a-8b, a temperature sensor 810 is provided in the opening 805 of the drive electrode 136 (in the figure shown as an example in the opening between the second row, fourth column and the fifth column of the electrodes). The area 812 corresponds to the drive electrode on the left side of the temperature sensor 810, the area 814 corresponds to the temperature sensor, and the area 816 corresponds to the drive electrode on the right side of the temperature sensor 810. For example, this temperature sensor 810 is located in the first electrode layer 183, and the temperature sensor 810 includes metal. For example, the temperature sensor 810 has a line width of 4 μm and a resistance of 1400Ω. For example, one end of wiring of the temperature sensor 810 is grounded, and the other end is connected to the binding area. For example, when the temperature sensor 810 is operating, a voltage of 5V is applied, and the resistance of the temperature sensor 810 is calculated by testing the current. Since the resistance of the metal is proportional to the temperature, when the temperature at the location of the temperature sensor 810 changes, its resistance changes accordingly, thereby obtaining the temperature. The temperature sensor 810 may be made of materials such as metal, alloy, conductive oxide, composite film layer, or other conductive materials. In some embodiments, the material of the drive electrode 170 and the temperature sensor 810 includes molybdenum. In some embodiments, the drive electrode 170 and the temperature sensor 810 may be formed by the same patterning process. Under some conditions (the line width is 4 μm, the resistance is 1400Ω, the 5V voltage is applied, and the material of the temperature sensor 810 includes molybdenum), after testing, the temperature resistance relationship of the temperature sensor 810 conforms to the following equation:

$$y = 3.31x + 1811.4 \qquad \text{formula (2)}$$

where y is the resistance and x is the temperature, so when the current test is completed, the temperature can be finally obtained through this formula (2).

Figure 10A:
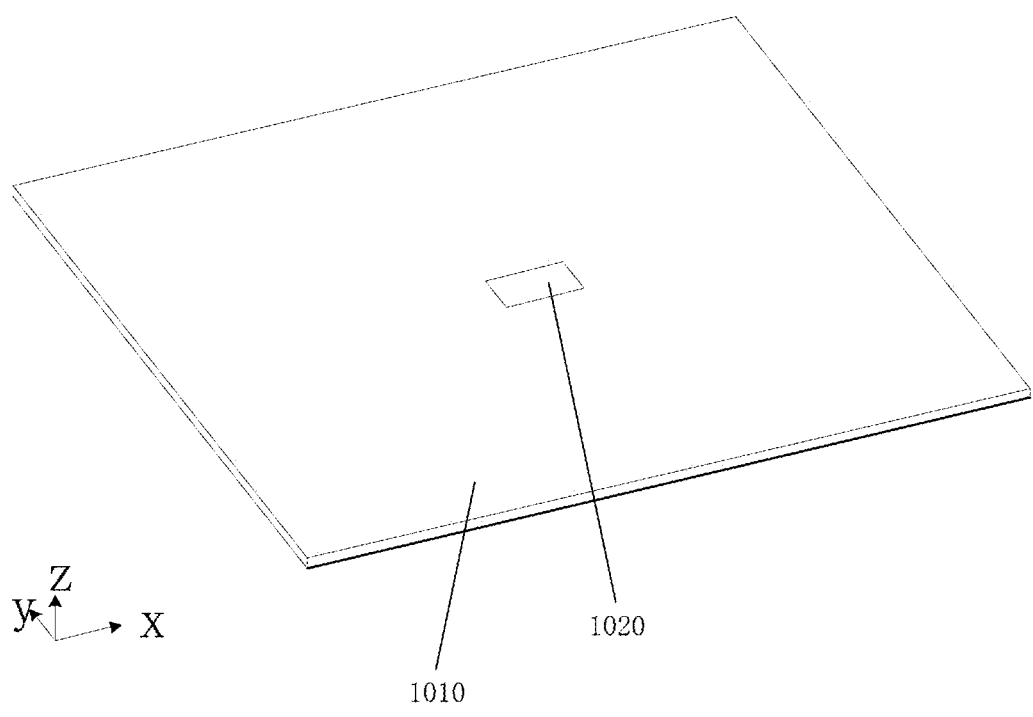
FIG. 10*a* schematically shows a model used for temperature simulation according to some embodiments of the present disclosure.
Figure 10B:
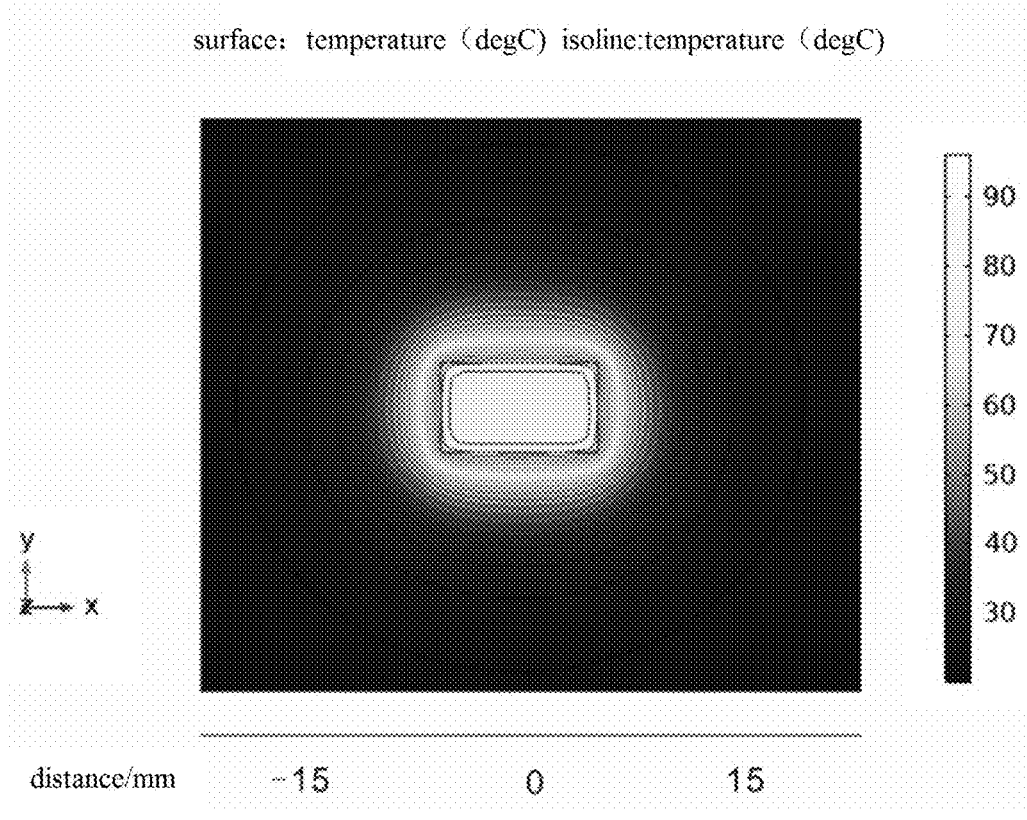
FIGS. 10*b*-10*c* schematically show simulation diagrams of temperature distribution according to FIG. 10*a;*
Figure 10C:
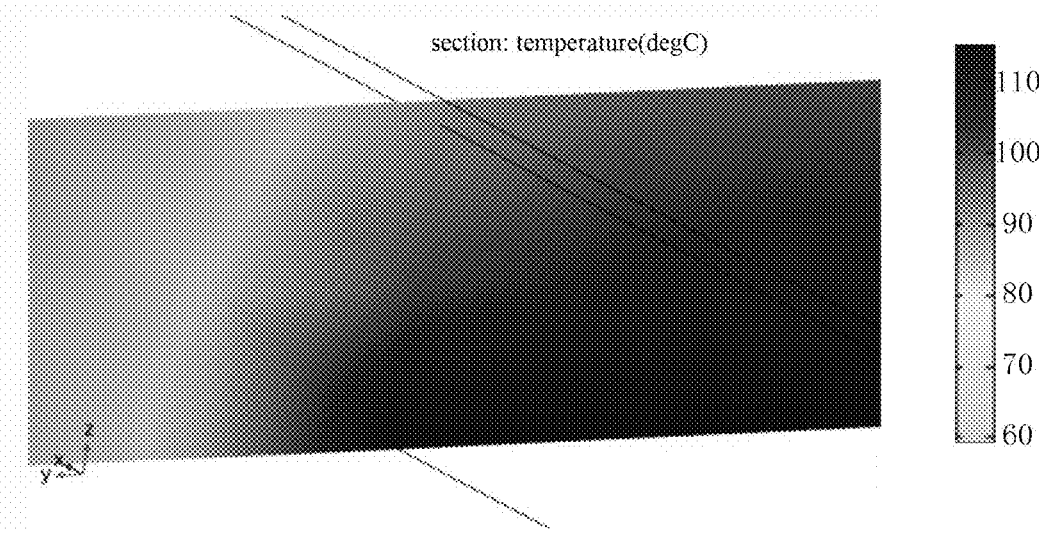

FIG. 10a schematically shows a model used for temperature simulation according to some embodiments of the present disclosure, and FIGS. 10b-10c schematically show simulation diagrams of temperature distribution according to FIG. 10a, where the model 1010 indicates the first substrate 102, the rectangular area 1020 corresponds to the temperature control area 130, and a heat source is arranged on the lower surface of the model 1010. The calculation shows that, as shown in FIG. 10b, when the temperature of the upper surface of the model 1010 reaches 95° C. required for temperature control preparation, the temperature at 15 mm from the center of the model 1010 (that is, the center of the rectangular area 1020) is about 25° C., which indicates that the temperature at about 1 cm from the temperature control area 130 is less affected by the temperature of the temperature control area. The nature of the reagent here will not be affected by the temperature of the temperature control area 130, so the distance between the temperature control area 130 and other functional areas can be set at no less than 1 cm.

FIG. 10c shows the temperature distribution of the cross section, which is taken along the approximate y-z plane as shown in FIG. 10a. Referring to FIG. 10a and FIG. 10c, the heat source is arranged on the lower surface of the model 1010, so the temperature near the lower surface is the highest. It can be seen from FIG. 10c that when the first dielectric layer 184 including polyimide is used, the temperature difference between the lower surface of the first substrate 102 and the upper surface of the hydrophobic layer 188 is about 10° C., and the temperature difference between the first electrode layer 183 and the upper surface of the hydrophobic layer 188 is about 1° C. When aluminum oxide with a thickness of 300 nm is used to make the first dielectric layer 184, the temperature difference between the first electrode layer 183 and the upper surface of the hydrophobic layer 188 is about 0.01° C. This is because the thermal conductivity of the aluminum oxide layer is 50 times that of the polyimide layer, and the thickness of the aluminum oxide layer is 1/127 of the thickness of the polyimide layer, which means that when the first dielectric layer 184 is made of aluminum oxide, the temperature measured by the temperature sensor 810 is very similar to the temperature of the lower surface of the fluid (droplet), the temperature control accuracy of the microfluidic device is greatly improved. It should be understood that due to different use environments or equipment environments, the thermal field distribution will change, and the thermal field calculation results will be different from the actual situation.

It can be seen from the above results that when the temperature sensor 810 is fabricated in the first electrode layer 183, the temperature sensor 810 is integrated and fabricated inside the first substrate 102, which reduces the distance between the droplet and the temperature sensor 810, thereby directly reflecting the temperature of the droplet. Such temperature control accuracy is greatly improved compared to the temperature control accuracy when the temperature sensor is fabricated on the lower surface of the first substrate 102 (that is, the temperature sensor is externally arranged). The preparation of the temperature sensor 810 in the first electrode layer 183 can avoid the inability to directly and objectively feedback the droplet temperature due to the external solution of the temperature sensor, thereby significantly improving the temperature control accuracy of the microfluidic device. Therefore, the first substrate 102 provided by the embodiment of the present disclosure can significantly improve the reliability of the microfluidic device in a high-temperature environment.

The first substrate 102 provided by the embodiments of the present disclosure may adopt different electrode designs for different functional areas, thereby improving the control accuracy of the fluid by the microfluidic device, such as fluid generation accuracy, temperature control accuracy, etc., thereby improving the performance of the microfluidic device, such as the accuracy of library preparation.

In some embodiments, referring to FIG. 2, the first substrate 102 may further include: a covering 176 on the drive electrode 170, and the covering 176 covers the surface of the drive electrode 170 except for the surface opposite to the first base substrate 180. For example, the material of the covering 176 includes ITO. Referring to FIG. 8b, the first substrate 102 further includes a covering 820 on the temperature sensor 810, and the covering 820 covers the surface of the temperature sensor 810 except for the surface opposite to the first base substrate 180. For example, the material of the covering 176 includes ITO. In some embodiments, the thickness of the covering may be 50 nm. The covering can completely cover the drive electrode 170 and the temperature sensor 810, thereby improving the reliability of the drive electrode 170 and the temperature sensor 810, and preventing the drive electrode 170 and the temperature sensor 810 from the problem of falling off during cleaning in the preparation process.

In some embodiments, referring to FIG. 2, the first substrate 102 may further include: a second electrode layer 174 between the first base substrate 180 and the first electrode layer 183; and an insulating layer 182 between the first electrode layer 183 and the second electrode layer 174. In some embodiments, the second electrode layer 174 includes a plurality of leads 175, and the drive electrode 170 in the first electrode layer 183 and the lead 175 corresponding to the drive electrode 170 are connected by a via hole 172, and the via hole 172 penetrates the insulating layer 182. In some embodiments, the thickness of the second electrode layer 174 may be 220 nm. The material of the lead 175 may be metal, alloy, conductive oxide, composite film layer, or other conductive materials, etc. In some embodiments, the material of the lead 175 includes molybdenum. In some embodiments, SiNx material can be selected for the insulating layer. In some embodiments, the thickness of the insulating layer may be 600 nm. Through the arrangement of the second electrode layer 174 including a plurality of leads 175 and the via hole 172 penetrating the insulating layer 182, the drive electrode 170 in the first electrode layer 183 can be electrically connected to a lead 175, and then electrically connected to other elements (for example, the bonding area) without arranging all wiring on the first electrode layer 183, which expands the wiring space and makes the volume of the first substrate 102 more compact.

In some embodiments, the driving of the drive electrode 170 may adopt various methods, such as active control, such as passive control. For passive control, there may not be a thin film transistor (TFT) directly corresponding to the drive electrode 170 in the first substrate 102, and a relay in the bonding area is used to generate a driving signal for control, thereby having a relatively large cost advantage.

In some embodiments, referring to FIG. 2, the first substrate 102 further includes: a second dielectric layer 186 between the first dielectric layer 184 and the first lyophobic layer 188. In some embodiments, the second dielectric layer 186 can be determined according to specific requirements as to whether it needs to be provided, and the material included in the second dielectric layer 186 can be selected as required. In some embodiments, when the microfluidic device is used for nucleic acid extraction, the second dielectric layer 186 can adopt an alkali-resistant parylene layer; and when the microfluidic device is used for library preparation, the second medium layer 186 can adopt a silicon oxide layer.

In some embodiments, for the detection or reaction that needs to apply strong alkaline reagents (such as NaOH), when the aluminum oxide layer is used as the first dielectric layer 184, it will react with such reagents, resulting in the damage of the first dielectric layer 184 and thus the failure of the first dielectric layer 184. Its reaction equation is as follows:

$$Al_2O_3 \quad + \quad 2NaOH \quad \longrightarrow \quad 2NaAlO_2 \quad + \quad H_2O$$

Therefore, in order to drive the strong alkaline reagents, a layer of second dielectric layer 186 that is resistant to alkali may be prepared on the first dielectric layer 184. In some embodiments, the second dielectric layer 186 includes a parylene layer. Correspondingly, when polyimide is used to fabricate the first dielectric layer 184, since polyimide does not react with a strong base, the second dielectric layer 186 may not be fabricated at this time. For example, the relative dielectric constant of the parylene layer may be 3.0, and the thickness may be 1 μm.

In some embodiments, when the second dielectric layer 186 is provided, the dielectric wetting effect can be described by the following equation:

$$\cos \theta = \cos \theta_0 + \frac{\varepsilon_0 \varepsilon_1 \varepsilon_2 \Delta V^2}{2(d_1 \varepsilon_2 + d_2 \varepsilon_1) \gamma_{l_g}}$$

where $\varepsilon_1$ is the relative dielectric constant of the first dielectric layer 184, $\varepsilon_2$ is the relative dielectric constant of the second dielectric layer 186, $d_1$ is the thickness of the first dielectric layer 184, and $d_2$ is the thickness of the second dielectric layer 186. Through the analysis of the above principles, the driving of the relevant reagents can be realized at 40 Vrms.

In some embodiments, in one or more functional areas located in the at least one functional area, the first lyophobic layer 188 is patterned so that the second dielectric layer 186 is periodically exposed. By periodically exposing the second dielectric layer 186, a part of the second dielectric layer 186 can be brought into contact with the droplets. Therefore, the properties of the second dielectric layer 186 can be set to achieve the modification of the surface of the first substrate 102 (at this time it is the patterned first hydrophobic layer) to achieve customized manipulation of the droplets.

In some embodiments, the material of the second dielectric layer 186 includes silicon oxide, particularly a silicon oxide layer prepared by an atomic layer deposition process.

Figure 11A:
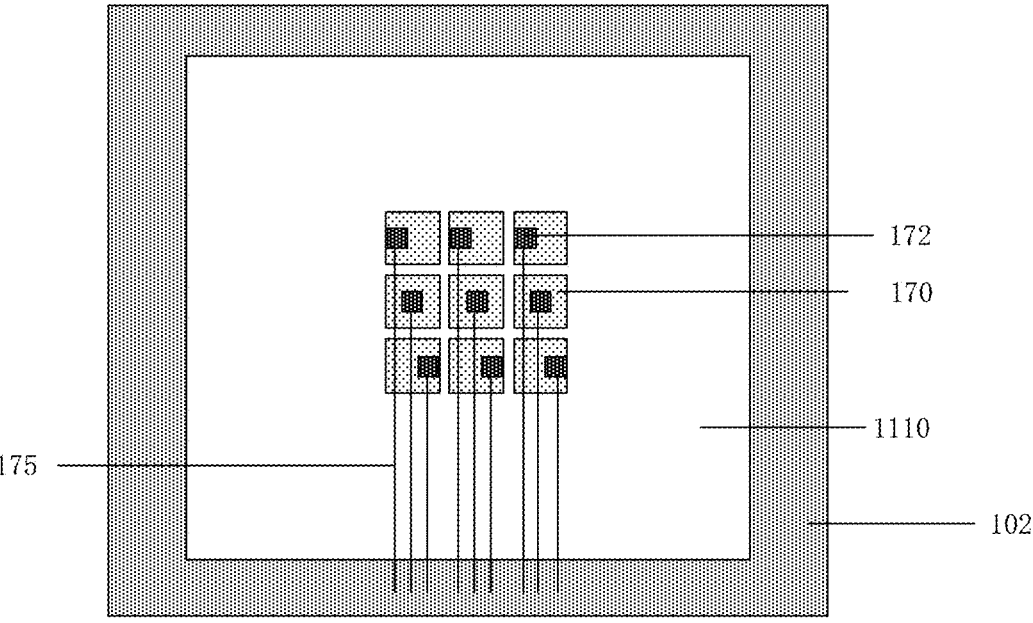
FIG. 11*a* shows a schematic structural view of a first substrate with a surface modification area according to some embodiments of the present disclosure.
Figure 11B:
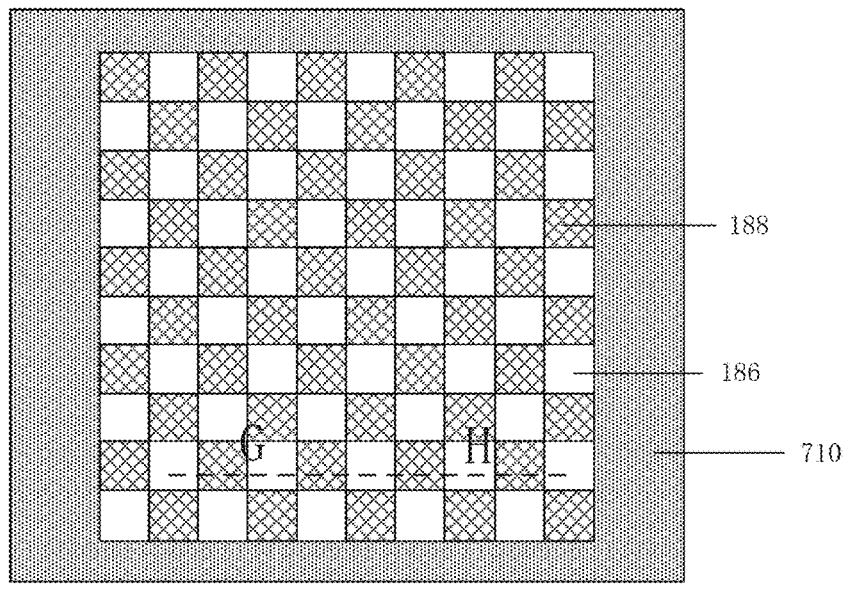
FIG. 11*b* shows a schematic diagram of a patterned first hydrophobic layer according to some embodiments of the present disclosure.
Figure 11C:
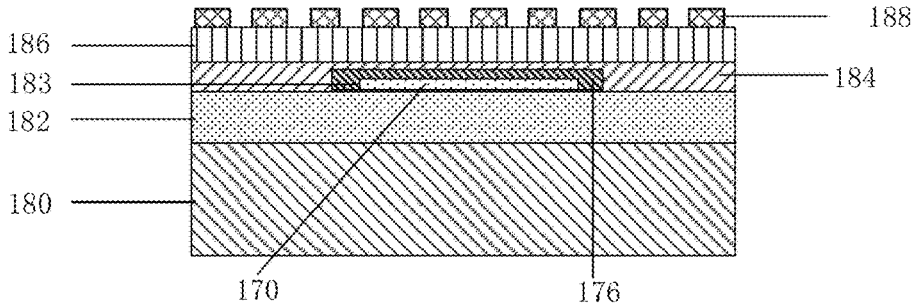
FIG. 11*c* shows a cross-sectional view of the first substrate according to some embodiments of the present disclosure, which is taken along the position shown by the line G-H in FIG. 11*b;*

FIG. 11a shows a schematic structural diagram of a first substrate 102 with a surface modification area according to some embodiments of the present disclosure. The first substrate 102 includes a plurality of drive electrodes 170, and the drive electrodes 170 are connected to the wirings 175 through the via holes 172, to realize the conduction between the drive electrodes 170 and the bonding area 115. For example, the cross-sections of the via holes 172 are shown as squares, and in some embodiments, they may also have other shapes such as circles. The area 1110 indicates the surface modification area, which is, for example, a patterned first hydrophobic layer, and the specific structure of the patterned first hydrophobic layer is shown in FIG. 11b. For detections or reactions that require surface modification or elution with magnetic beads, as shown in FIGS. 11b-11c, the first hydrophobic layer 188 can be patterned in the detection area 710 so that the second dielectric layer 186 is periodically exposed. The exposed size of the second dielectric layer 186 is, for example, 4 μm*4 μm square for chemical modification or DNA capture and release. This structure can be used in a washing process, such as the washing process in the library construction process, and its working principle is as follows. Hydrogen bonds are easily formed between DNA single-stranded molecules and the surface of silicon oxide, and the hydrogen bonding force is far greater than the electrostatic repulsion between DNA and the surface of silicon oxide, and when the pH of the reagent system is lower than the Pka value of the silica surface (PH 6.7), its electrostatic repulsion will be further reduced, so DNA will be adsorbed to the surface of silicon oxide. When a low-strength ion buffer with a pH value greater than 8.0 is used to elute the surface of the silicon oxide absorbed with DNA, the electrostatic repulsion on the surface will increase, causing the hydrogen bond between the DNA molecular chain and the surface of silicon oxide to break and realizing DNA elution. This method can save the use of magnetic beads in the reagent and the use of the magnetron module in the drive system.

In some embodiments, the thickness of the second dielectric layer 186 including the silicon oxide layer is 300 nm. In some embodiments, the silicon oxide layer is made by the following principle: the precursor including $(C_2H_5)_4SiN_2H_2$ and $O_3$, and the reaction equation being $2(C_2H_5)_4SiN_2H_2+2O_3 \rightarrow 2SiO_2+O_2+4HN(C_2H_5)_2$.

The first substrate 102 provided by the embodiments of the present disclosure can adopt different film layer designs for different functional areas, thereby improving the control accuracy of the fluid by the microfluidic device, such as fluid generation accuracy, temperature control accuracy, etc., thereby improving the performance of the microfluidic device, such as the accuracy of library preparation.

In some embodiments, the first base substrate may be a PCB base substrate, and the surface roughness of the PCB base substrate is relatively large, generally about 0.5 μm, which may lead to a relatively large surface resistance, thereby limiting the movement speed of the droplets. The stable driving speed of the PCB base substrate may be about 0.5 mm/s. In some embodiments, the first base substrate 180 may include glass. The roughness of the glass base substrate (approximately 0.01 μm) is about ⅟₅₀ of that of the PCB base substrate, and the steady driving speed of the droplets of the glass base substrate can reach about 10 mm/s.

Figure 12:
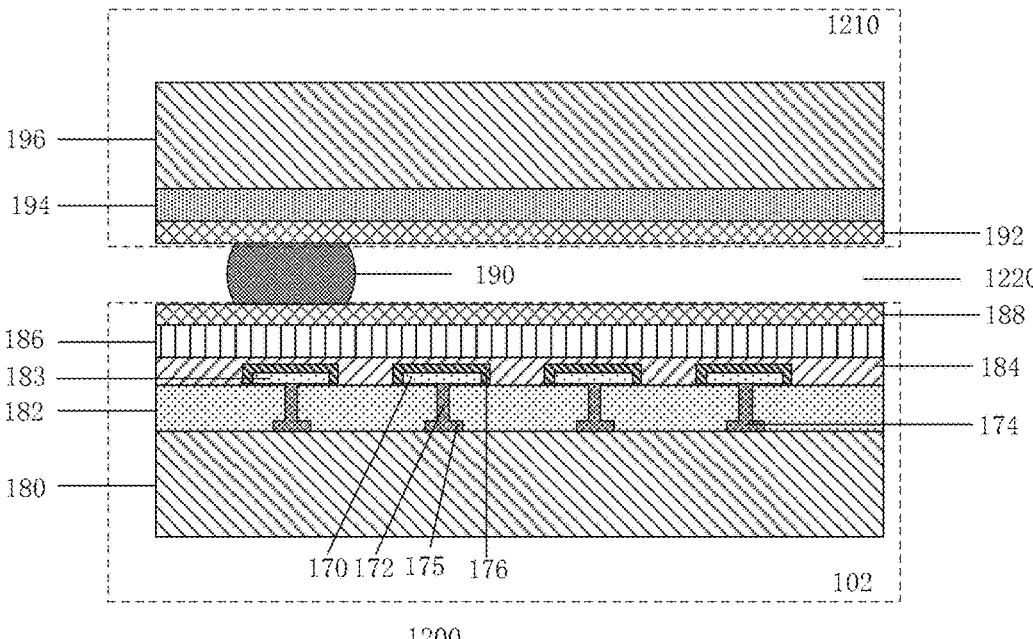
FIG. 12 shows a cross-sectional view of a microfluidic device according to some embodiments of the present disclosure, the cross-sectional view being taken along the same cross-section as FIG. 2.

The embodiments of the present disclosure also provide a microfluidic device. FIG. 12 shows a cross-sectional view of a microfluidic device according to some embodiments of the present disclosure, the cross-sectional view being taken along the same cross-section as FIG. 2. The microfluidic device 1200 includes a first substrate 102 according to any one of the first substrates as described above, and a second substrate 1210 assembled with the first substrate 102. The second substrate 1210 includes: a second base substrate 196; a conductive layer 194 on the second base substrate; and a second lyophobic layer 192 on the side of the conductive layer away from the second base substrate. In some embodiments, a space 1220 is defined between the first substrate 102 and the second substrate 1210. The droplet 190 may be driven by the drive electrode 170 to move in the space 1220. In some embodiments, the space 1220 may be filled with air. In some embodiments, the space 1220 may be filled with silicone oil or the like without contaminating the droplets, and the silicone oil may be used as a lubricant. In some embodiments, the conductive layer 194 of the second substrate 1210 can be made of ITO or PEDOT material. For example, the sheet resistance of the conductive layer 194 is less than 200 Ω/Squ. In some embodiments, the second lyophobic layer 192 may include the same material as the first lyophobic layer 188.

Figures 13A, 13B:
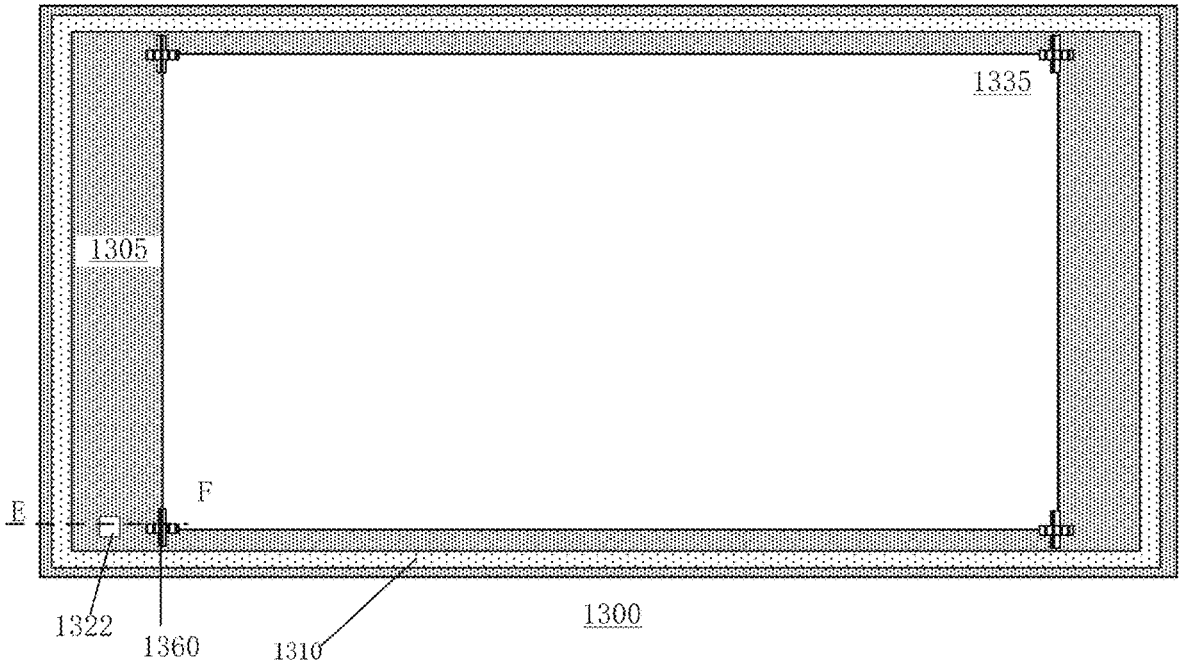

FIG. 13a schematically shows the surface of the first substrate opposite to the second substrate of the microfluidic device 1300 according to some embodiments of the present disclosure. FIG. 13b schematically shows a cross-sectional view of a microfluidic device according to some embodiments of the present disclosure, which is taken along the position shown by the line E-F in FIG. 13a.

In some embodiments, referring to FIGS. 1 and 13a-13b, the first substrate 102 includes a peripheral area 1305 and an operation area 1335. The peripheral area 1305 may include a ground electrode area 1310. In some embodiments, as shown in FIGS. 1 and 13a, the ground electrode area 1310 has a ring shape. In some embodiments, the ground electrode area 1310 is provided with a ground electrode 1350, and the conductive layer 194 of the second substrate 1210 is electrically connected to the ground electrode 1350. In this way, the conductive layer 194 of the second substrate 1210 can be grounded, so that the drive electrode 170 can drive the droplet 190. The second substrate is grounded through the peripheral ground electrode of the first substrate, which improves the grounding stability of the second substrate.

In some embodiments, the conductive layer 194 is electrically connected to the ground electrode 1350 through the conductive cotton 1340 to realize the grounding function of the second substrate 1210. In some embodiments, the ground electrode 1350 is covered with a covering 1352, and the covering 1352 is located between the ground electrode 1350 and the conductive cotton 1340. For example, the material of the covering 1352 includes ITO.

In some embodiments, referring to FIGS. 13a-13b, the area 1320 is a two-dimensional code preparation area, which includes a mark 1322 (for example, a two-dimensional code). The production information of the microfluidic device can be tracked through the preparation of the two-dimensional code. Since lasers are required for the production of the two-dimensional code, this area is not covered by the covering 1352.

In some embodiments, referring to FIGS. 13a-13b, the area 1330 includes alignment marks 1360 for making the first lyophobic layer 188, the first dielectric layer 184, and the second dielectric layer 186. For example, the first lyophobic layer 188, the first dielectric layer 184, and the second dielectric layer 186 cover the middle area of the four cross-shaped alignment marks 1360, so that they can be well aligned. Through the alignment design, the preparation accuracy of the first lyophobic layer 188, the first dielectric layer 184, and the second dielectric layer 186 can be improved.

In some embodiments, one or more of the first lyophobic layer 188, the first dielectric layer 184, the second dielectric layer 186, and the insulating layer 182 are kept clear of the cutting width during the cutting of the first base substrate 180. For example, the end surface of the insulating layer 182 is no less than 150 μm away from the end surface of the first base substrate 180. That is, in the peripheral area 1305, the distance between the projection of the insulating layer 182 on the first base substrate 180 and the cutting surface 1801 of the first base substrate 180 is no less than 150 μm.

The microfluidic device has similar characteristics and technical effects to the above-mentioned microfluidic substrate, and will not be repeated here.

The embodiments of the present disclosure also provide a driving method for a microfluidic device. The microfluidic device 1200 includes a first substrate 102 according to any one of the first substrates as described above, and a second substrate 1210 assembled with the first substrate 102. The second substrate 1210 includes: a second base substrate 196; a conductive layer 194 on the second base substrate; and a second lyophobic layer 192 on the side of the conductive layer 194 away from the second base substrate 196. In some embodiments, a space 1220 is defined between the first substrate 102 and the second substrate 1210.

Figures 14C, 14D:
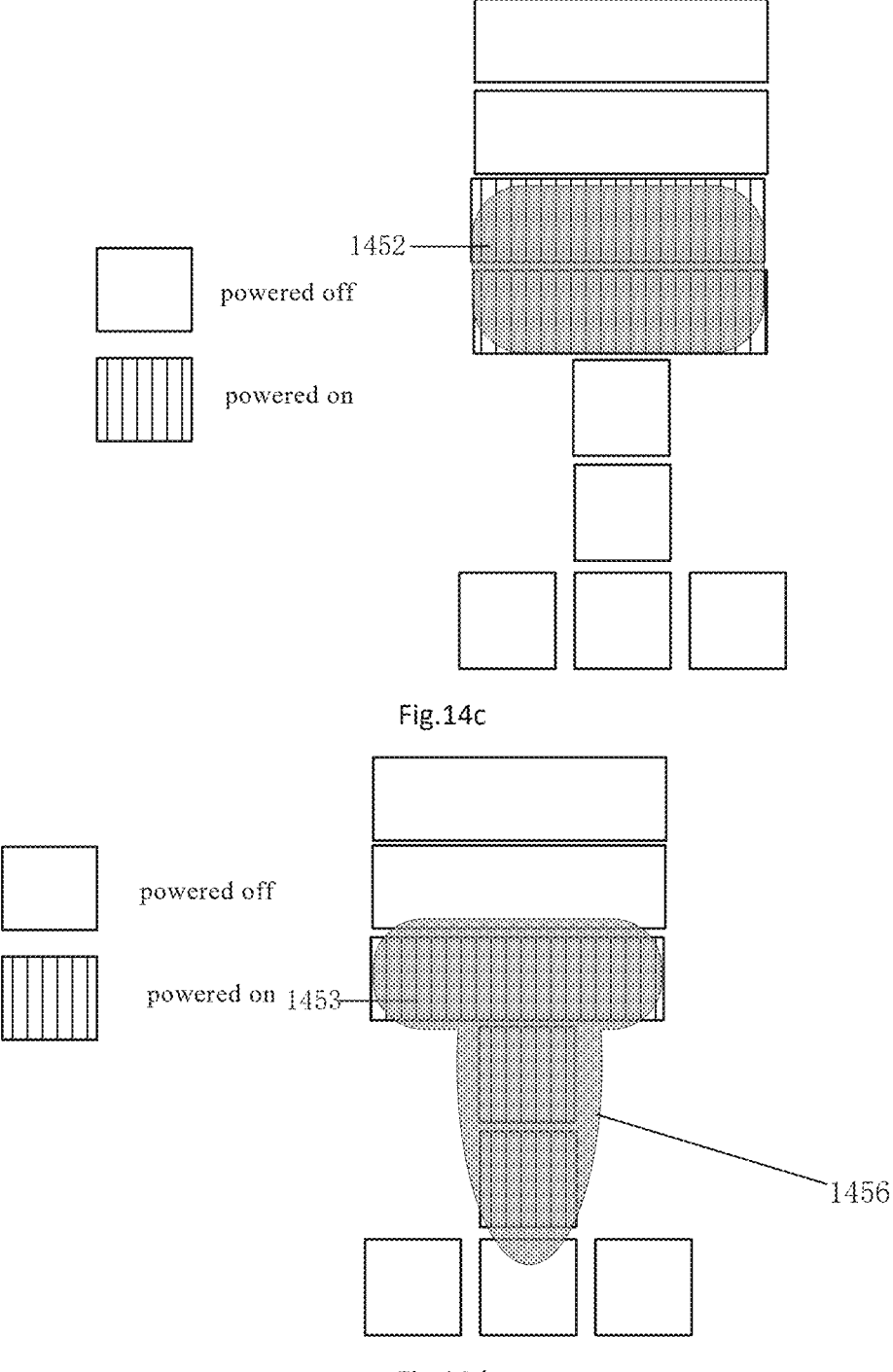

FIG. 14a schematically shows a flowchart of a driving method 1400 according to some embodiments of the present disclosure. FIGS. 14b-14m schematically show a driving process for the reagent area 112 according to some embodiments of the present disclosure. In some embodiments, for the reagent area 112, referring to FIGS. 3a and 14a-14e, the driving method 1400 may include steps S1410-S1440.

S1410, controlling the reagent area liquid storage portion 204 to perform sample injection of the reagent area liquid storage portion 204 (as shown by 1451 in FIG. 14b). For example, the droplets are directly injected into the reagent area liquid storage portion 204 by a pipette when the electrodes included in the reagent area liquid storage portion 204 are powered on.

Figures 14E, 14F:
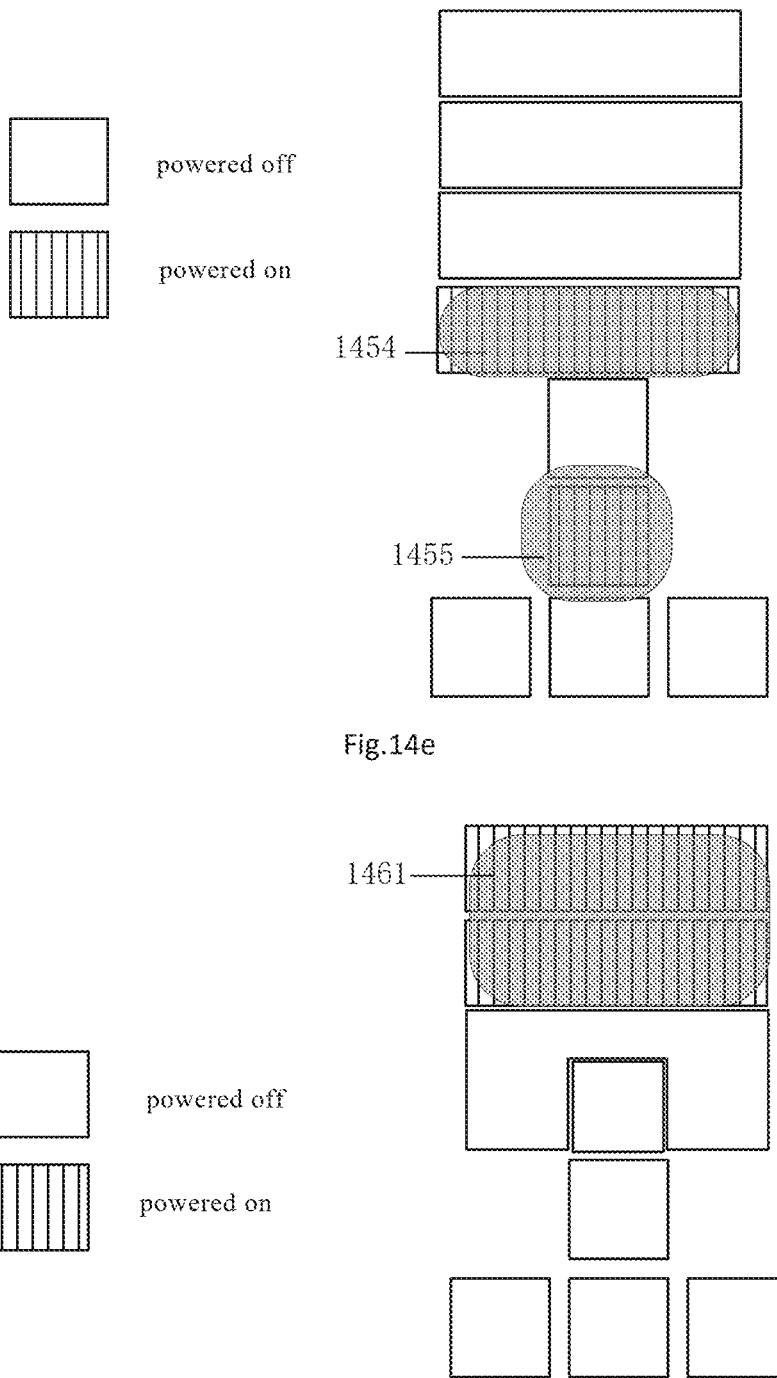
Figures 14G, 14H, 14I:
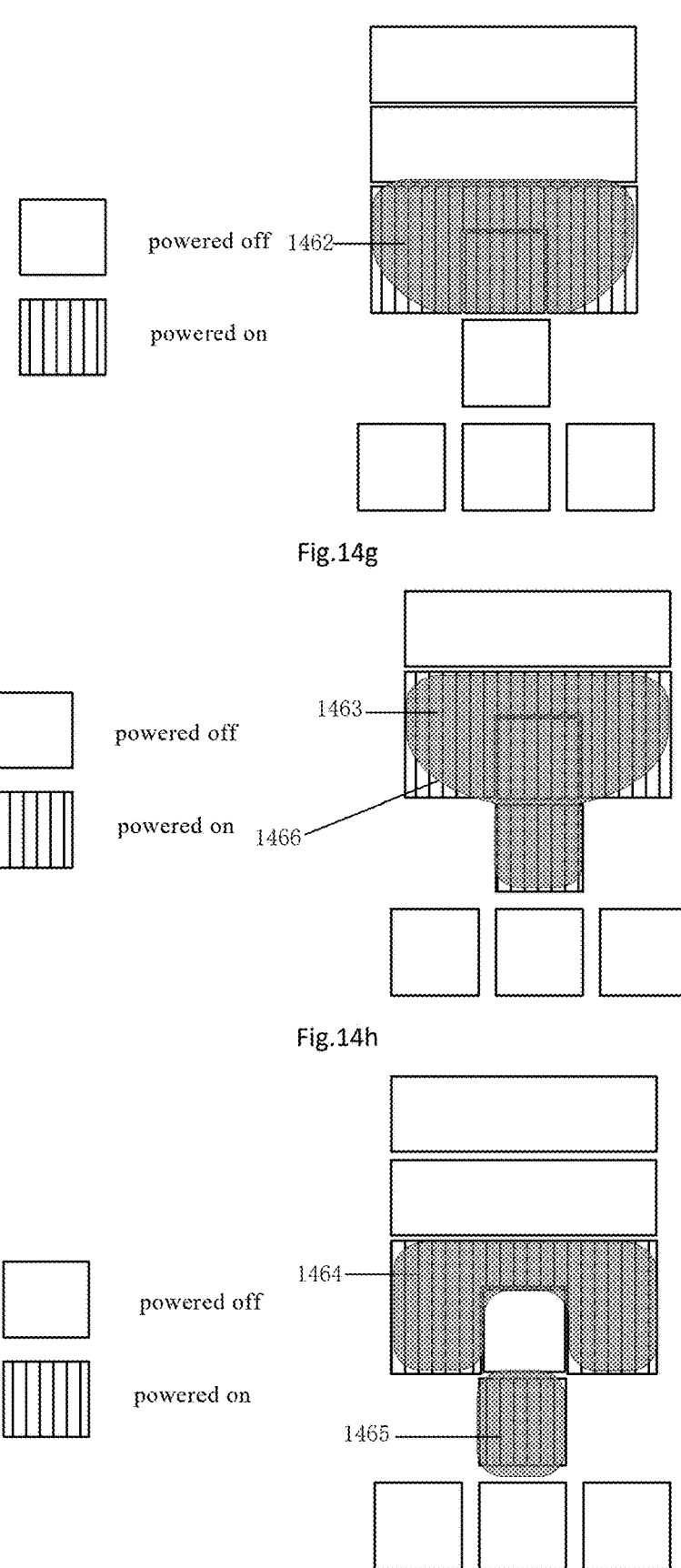
Figures 14J, 14K:
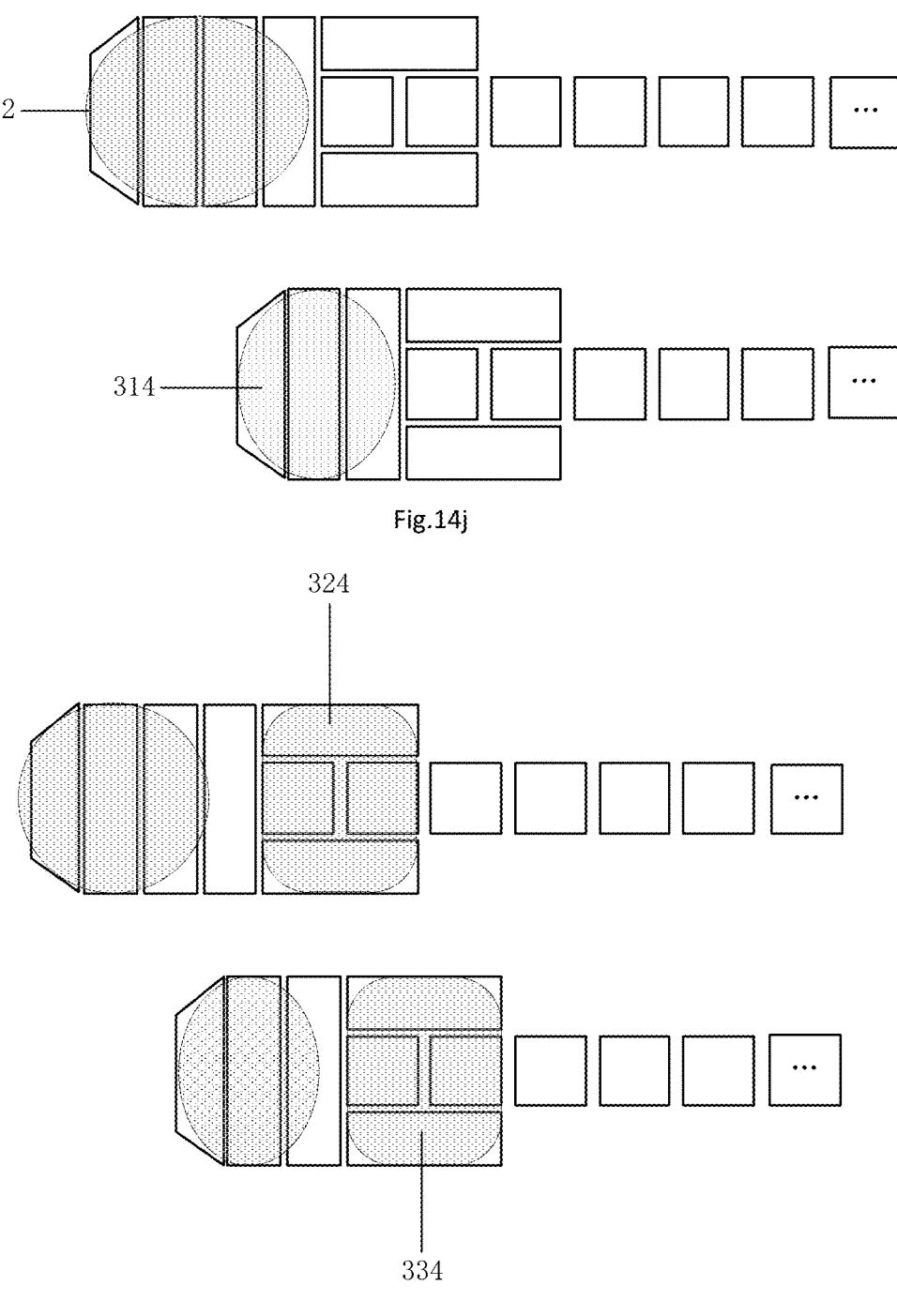
Figure 14L:
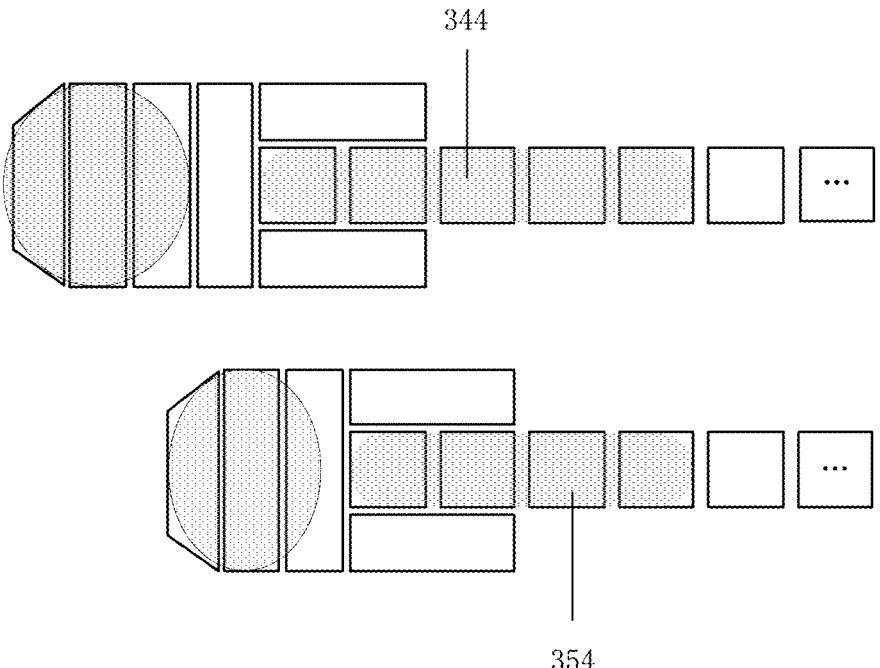
Figure 14M:
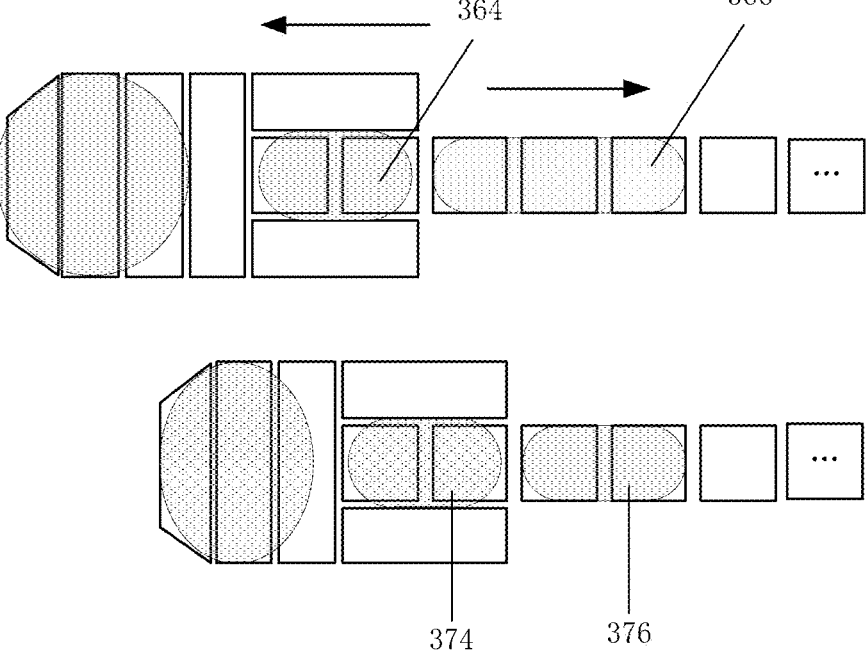

S1420, controlling the reagent area liquid storage portion 204 and the droplet shape changing portion 205 to generate an intermediate droplet from the reagent area liquid storage portion 204 that covers the droplet shape changing portion 205 (as shown by 1452 in FIG. 14c);

S1430, controlling the droplet shape changing portion 205 and the reagent area flow channel 206 to change the shape of the intermediate droplet (as shown by 1453 in FIG. 14d); and S1440, controlling the droplet shape changing portion 205 or the reagent area flow channel 206 to generate a reagent droplet in the reagent area flow channel 206 (as shown by 1454 and 1455 in FIG. 14e).

Specifically, as shown in FIGS. 14b-14e, for the reagent area shown in FIG. 3a, the driving process may include the following steps:

powering on the drive electrodes 2044 and 2042 to perform sample injection 1451 of the reagent area liquid storage portion 204;

powering off the drive electrodes 2044 and 2042, and powering on the drive electrodes 2054 and 2052 to generate an intermediate droplet 1452 from the reagent area liquid storage portion 204 that covers the droplet shape changing portion 205;

powering off the drive electrode 2054, and powering on the drive electrodes 2052, 2062, 2064 to change the shape of the intermediate droplet 1452, and the changed droplet is 1453; and powering off the drive electrode 2062 to generate a reagent droplet 1455 in the reagent area flow channel 206, where the remaining part of the intermediate droplet 1453 is labeled as 1454.

Through the driving method 1400, the sample injection of the reagent area and the generation of reagent droplets can be realized. This driving method has advantages and effects similar to those described above with respect to FIG. 3a, and will not be repeated here.

In some embodiments, the specific arrangement of the electrodes in the reagent area 112 may be the same as or similar to that shown in FIG. 3b. In some embodiments, the step S1430 may include: powering on the first electrode module 2056, the second electrode module 2058, and the drive electrode 2066 of the reagent area flow channel 206 to change the shape of the intermediate droplet. The step S1440 may include: powering off the second electrode module 2058 to generate the reagent droplet in the reagent area flow channel 206. Specifically, for the reagent area shown in FIG. 3b, as shown in FIGS. 14f-14i, the driving process may include the following steps:

powering on the drive electrodes 2044 and 2042 to perform sample injection 1461 of the reagent area liquid storage portion 204;

powering off the drive electrodes 2044 and 2042, and powering on the first electrode module 2056 and the second electrode module 2058 to generate an intermediate droplet 1462 from the reagent area liquid storage portion 204 that covers the droplet shape changing portion 205;

powering on (the first electrode module 2056, the second electrode module 2058, and) the drive electrode 2066 of the reagent area flow channel 206, to change the shape of the intermediate droplet 1462, and the changed droplet is 1463; and powering off the second electrode module 2058 to generate a reagent droplet 1465 in the reagent area flow channel 206, where the remaining part of the intermediate droplet 1463 is labeled as 1464.

Through the driving method, the sample injection of the reagent area and the generation of reagent droplets can be realized. This driving method has advantages and effects similar to those described above with respect to FIG. 3b, and will not be repeated here. In particular, in FIG. 14d, the shape of the intermediate droplet 1452 changes, and the changed droplet is 1453. When the shape of the intermediate droplet 1453 changes, an elongated stretched part will be produced. There is an arc-shaped solitary area 1456 between the elongated stretched part and the main body part, and the projected area of the arc-shaped solitary area 1456 on the first base substrate exceeds the projected area of the drive electrodes 2062, 2064 on the first base substrate. This may cause the projected area of the reagent droplet 1455 on the first base substrate to be larger than the projected area of the drive electrode 2064 on the first base substrate when the reagent droplet 1455 is being generated on the reagent area flow channel 206, resulting in the volume of the generated reagent droplet 1455 is not accurate. Correspondingly, in FIG. 14*h*, the arc-shaped solitary area 1466 exists inside the reagent area 112, so as not to affect the projected area of the generated reagent droplet 1465 on the first base substrate, thereby improving the accuracy and stability of droplet generation.

In particular, for the reagent area shown in FIG. 3*b*, in some embodiments, an overall shape of the drive electrodes 2054, 2052 (or 2056, 2058) included in the droplet shape changing portion 205 is a rectangle with two sides perpendicular to an extending direction of the reagent area channel 206. The two corners 2046 and 2018 of the rectangle on a side close to the reagent area flow channel may be provided with chamfers. The specific manner of setting each chamfer can be similar to that for the first electrode 210, and will not be repeated here. The electric field formed by using the chamfered electrode here has a better matching with the actual shape of the droplets 1462, 1463, 1464 in each stage in the reagent droplet generation process, which can the step S1430 may include: powering off the sixth electrode 260 and the seventh electrode 270 and powering on the eighth electrode 280; and powering on the ninth electrode 290 to change the shape of the intermediate droplet (as shown by 344 in FIG. 14*l*, and as shown by 354 in FIG. 14*l* for the reagent area 122 in FIG. 3*c*). In some embodiments, the step S1440 may include: powering off the fifth electrode 250 to generate the reagent droplet in the reagent area flow channel 126 (as shown by 364 and 366 in FIG. 14*m*; and as shown by 374 and 376 in FIG. 14*m* for the reagent area 122 in FIG. 3*c*, where the arrows respectively indicate the moving to directions of different droplets). In some embodiments, for the reagent area 122, the on-off state (power-on and power-off steps) of the additional electrode 225 may be consistent with that of the first electrode 210.

The following table shows the on-off states of different drive electrodes during the driving process for the reagent area 112 as discussed above (where "√" means "on" and "x" means "off").

| step | Corresponding FIG. | 210 | 220 | 230 | 260/270 | 240 | 250 | 280 | 290 | process |
|------|------|------|------|------|------|------|------|------|------|------|
| S1410 | 14j | ✓ | ✓ | ✓ | x | x | x | x | x | sample injection |
| S1420 | 14k | x | x | x | ✓ | ✓ | x | x | x | generating an |
| S1420 | 14k | x | ✓ | ✓ | ✓ | ✓ | x | x | x | intermediate droplet |
| S1420 | 14k | ✓ | ✓ | x | ✓ | ✓ | ✓ | x | x | from the reagent area liquid storage portion that covers the fourth electrode, the fifth electrode, the sixth electrode, and the seventh electrode |
| S1430 | 14l | ✓ | ✓ | x | x | ✓ | ✓ | ✓ | x | the shape of the |
| S1430 | 14l | ✓ | ✓ | x | x | ✓ | ✓ | ✓ | ✓ | intermediate droplet changes |
| S1440 | 14m | ✓ | ✓ | x | x | ✓ | x | ✓ | ✓ | generating the reagent droplet in the reagent area flow channel | improve the accuracy of electrode control, thereby improving the accuracy and stability of droplet generation.

In some embodiments, the specific arrangement of the electrodes in the reagent area 112 and the reagent area 122 may be the same as or similar to that shown in FIG. 3*c*. The following takes the reagent area 112 in FIG. 3*c* as an example to specifically describe the driving method 1400 according to some embodiments. In some embodiments, the step S1410 may include: powering on the first electrode 210, the second electrode 220, and the third electrode 230 to perform the reagent sample injection of the reagent area liquid storage portion 114 (as shown by 312 in FIG. 14*j*, and as shown by 314 in FIG. 14*j* for the reagent area 122 in FIG. 3*c*). In some embodiments, the step S1420 may include: powering off the first electrode 210, the second electrode 220, and the third electrode 230 and powering on the fourth electrode 240, the sixth electrode 260, and the seventh electrode 270; powering on the second electrode 220 and the third electrode 230; powering off the third electrode 230, and simultaneously powering on the fifth electrode 250, the sixth electrode 260, the seventh electrode 270, the first electrode 210, and the second electrode 220 to generate an intermediate droplet from the reagent area liquid storage portion 114 that covers the fourth electrode 240, the fifth electrode 250, the sixth electrode 260, and the seventh electrode 270 (as shown by 324 in FIG. 14*k*, and as shown by 334 in FIG. 14*k* for the reagent area 122 in FIG. 3*c*). In some embodiments, Through this driving method, the sample injection of the reagent area and the generation of reagent droplets can be realized. This driving method has advantages and effects similar to those described above with respect to FIG. 3*c*, and will not be repeated here.

Figure 15A:
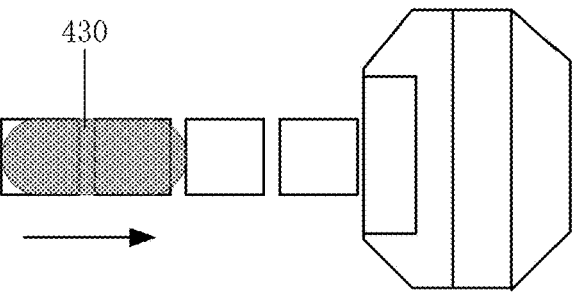
FIGS. 15a-15c schematically show a driving process for a waste liquid area according to some embodiments of the present disclosure.
Figure 15B:
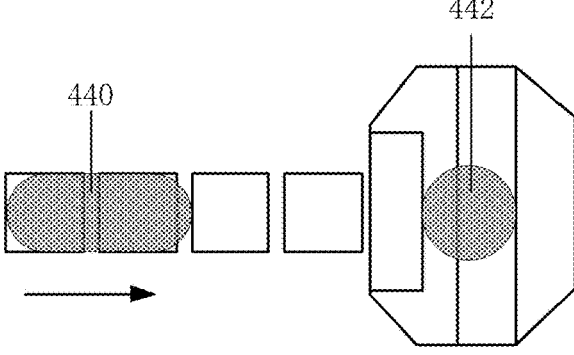
Figure 15C:
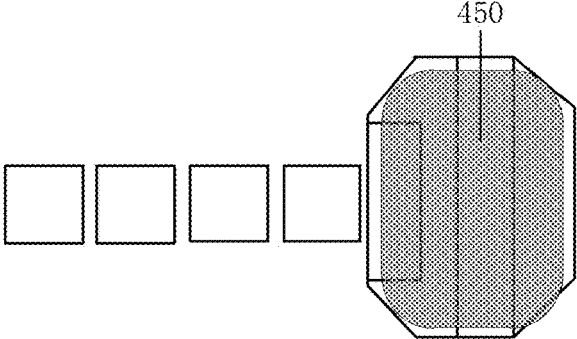

FIGS. 15*a*-15*c* schematically illustrate a driving process for a waste liquid area according to some embodiments of the present disclosure. Referring to FIGS. 4 and 15*a*-15*c*, in some embodiments, the driving method for the waste liquid area may include: driving the droplet 430 from other functional areas (such as the temperature control area 130) to the waste liquid area 160 (as shown in FIG. 15*a*); controlling the drive electrodes included in the waste liquid area transition portion 412 to move the droplet to the middle position of the waste liquid area liquid storage portion 411 (indicated by 442), while there may be other droplets 440 driven to the waste liquid area 160 (as shown in FIG. 15*b*); and finally gathering a plurality of droplets 450 to the waste liquid area liquid storage portion 411. Through this driving method, droplet collection in the waste liquid area can be achieved. This driving method has advantages and effects similar to those described above with reference to the waste liquid area 160 of the first substrate 102, and will not be repeated here.

Figure 16A:
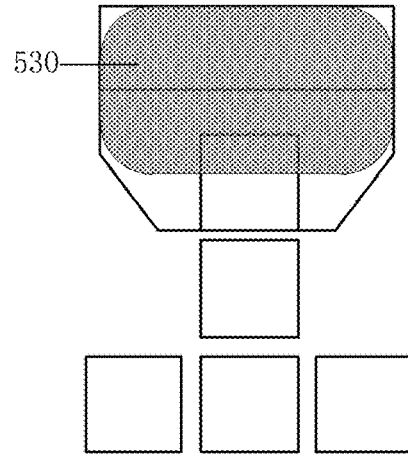
Figures 16B, 16C, 17A:
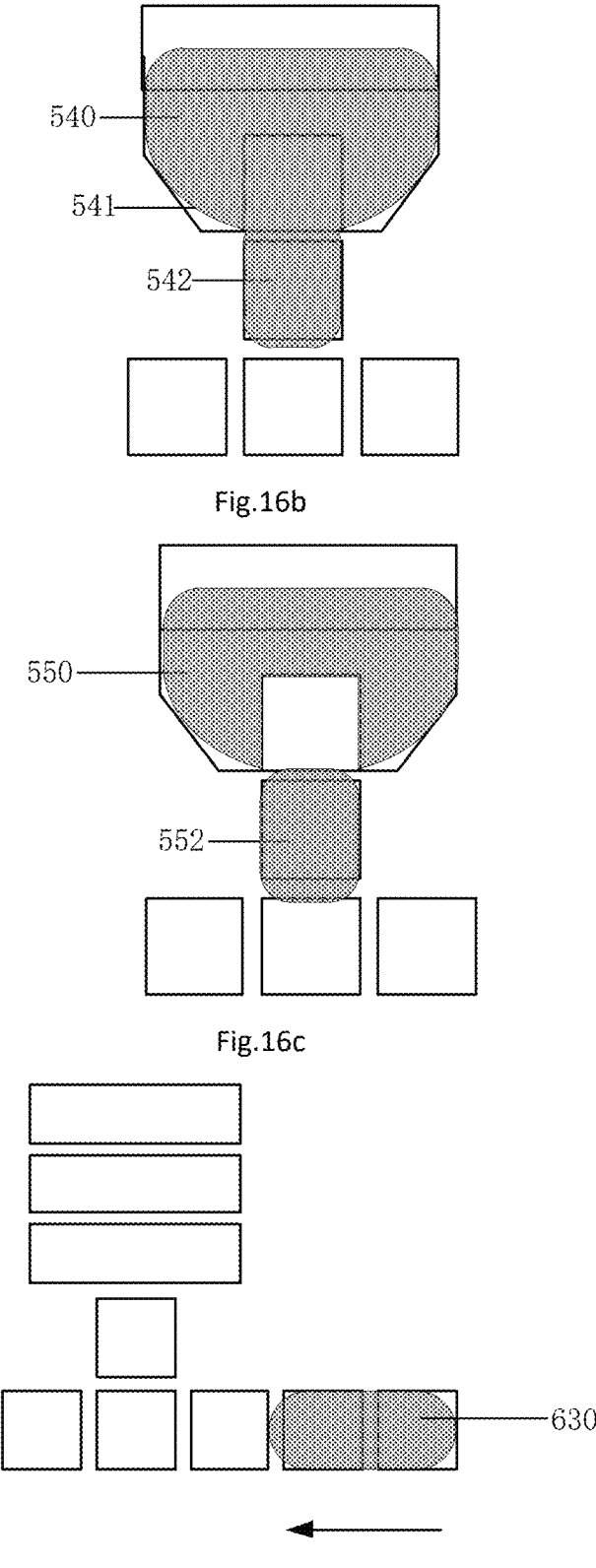

FIGS. 16*a*-16*c* schematically show the driving process for the sample inlet area according to some embodiments of the present disclosure. Referring to FIGS. 5 and 16*a*-16*c*, in some embodiments, the driving method for the sample inlet area may include: injecting a large droplet 530 into the sample inlet area (as shown in FIG. 16*a*); controlling the drive electrodes included in the sample inlet area transition portion 512 so that the intermediate droplet 540 generates an elongated stretched part 542 (as shown in FIG. 16*b*, there is an arc-shaped solitary area 541 between the elongated stretched part 542 and the main body part of the intermediate droplet 540, the arc-shaped solitary area 541 exists inside the sample inlet area, so as not to affect the projected area of the generated sample droplets on the first base substrate); and controlling the drive electrodes included in the sample inlet area transition portion 512 (for example, powering off the 1 mm*1 mm square electrode 532) to realize the splitting of large droplets and complete the generation of small droplets (such as sample droplets) 552 (as shown in FIG. 16*c*, where the remaining part of the intermediate droplet 530 is labeled as 550. The electric field formed by using the chamfered electrode here has a better matching with the actual shape of the droplet 540, 550 in each stage in the droplet generation process in the sample inlet area). With this driving method, the droplet with a small volume (for example, 1 μL) can be accurately generated. This driving method has advantages and effects similar to those described above with reference to the sample inlet area 140 of the first substrate 102, and will not be repeated here.

Figures 17B, 17C, 18A:
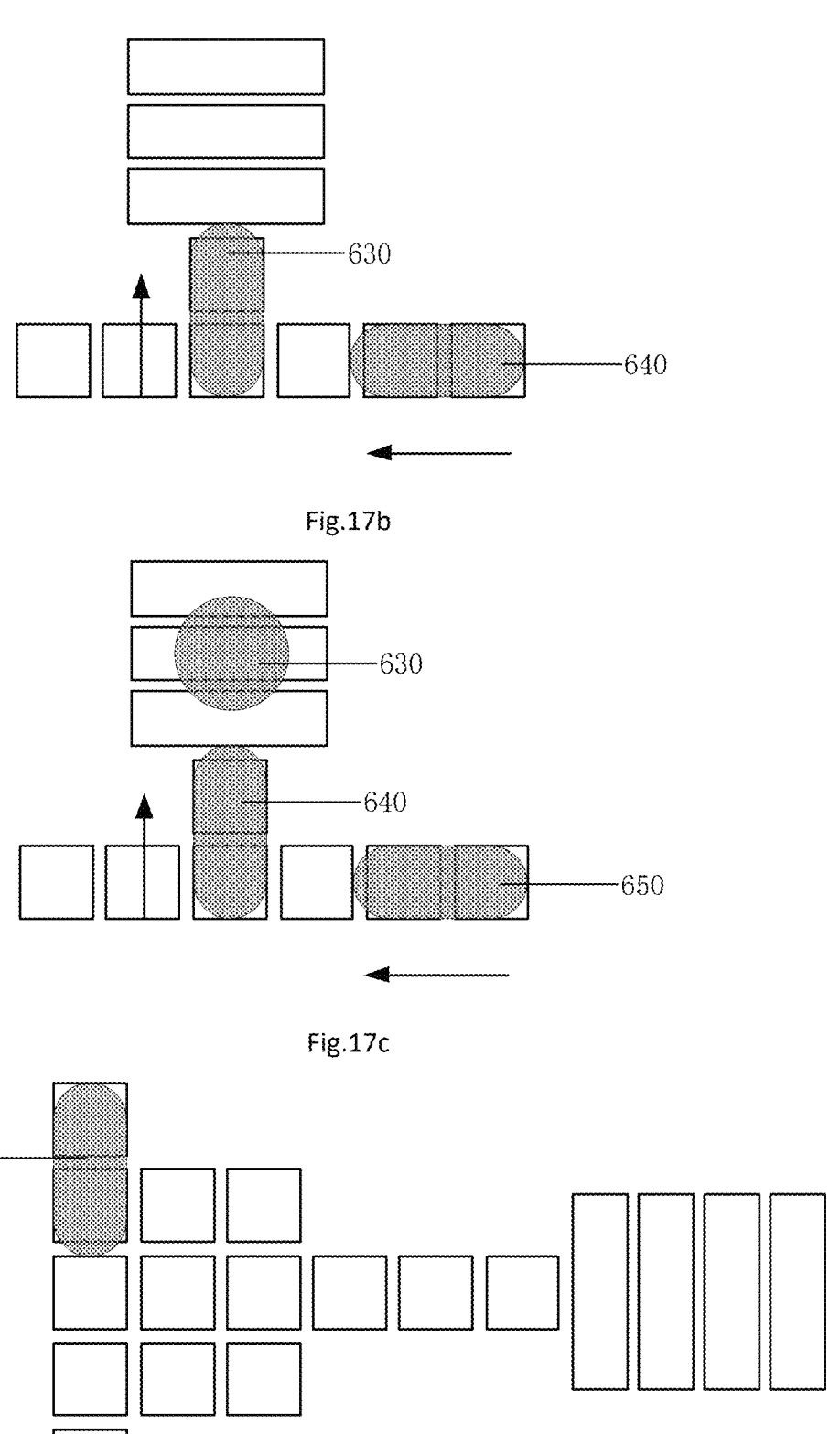

FIGS. 17*a*-17*c* schematically show a driving process for a sampling area according to some embodiments of the present disclosure. Referring to FIGS. 6 and 17*a*-17*c*, in some embodiments, the driving method for the sampling area may include: driving the droplet 630 from other functional areas (such as the temperature control area 130) to the sampling area 120 (as shown by the arrow in FIG. 17*a*); controlling the drive electrodes included in the sampling area 120 and the sampling area flow channel 121 to move the droplet 630 to the sampling area flow channel 121, while there may be other droplets 640 driven to the sampling area 120 (as shown in FIG. 17*b*); and controlling the drive electrodes included in the sampling area 120 and the sampling area flow channel 121 to move the droplet 630 to the middle position of the sampling area 120, while the droplet 640 may move to the sampling area flow channel 121 and there may be other droplets 650 driven toward the sampling area 120 (as shown in FIG. 17*c*). Through this driving method, droplet collection in the sampling area 120 can be achieved. For example, when the library construction is completed, the droplets move from the temperature control area 130 to the sampling area 120, and the size of the droplets is 1-3 μL, and are finally gathered in the sampling area 120. This driving method has advantages and effects similar to those described above with reference to the sampling area 120 of the first substrate 102, and will not be repeated here.

FIGS. 18*a*-18*c* schematically show a driving process for a quality detection area according to some embodiments of the present disclosure. Referring to FIGS. 7 and 18*a*-18*c*, in some embodiments, the driving method for the quality detection area 150 may include: driving the droplet 740 from other functional areas to the quality detection area 150 (as shown in FIG. 18*a*); completing the detection in the detection area (for example, the optical detection area) 710 (as shown in FIG. 18*b*); after the detection is completed, driving the droplet 740 to the quality detection area waste liquid portion 730 (as shown in FIG. 18*c*). In some embodiments, the waste liquid can be taken out of the microfluidic device from the quality detection area waste liquid portion 730. This driving method has advantages and effects similar to those described above with reference to the quality detection area 150 of the first substrate 102, and will not be repeated here.

The embodiments of the present disclosure also provide a method of manufacturing a first substrate for a microfluidic device. FIG. 19 schematically shows a flowchart of a method 1900 for manufacturing a first substrate for a microfluidic device according to some embodiments of the present disclosure. As shown in FIG. 19, the method 1900 includes S1910 preparing a first base substrate; and S1920 preparing a first electrode layer on the base substrate, the first electrode layer including a plurality of drive electrodes, wherein the plurality of drive electrodes define at least one flow channel and at least one functional area in the first substrate, the at least one functional area includes a reagent area, the at least one flow channel includes a reagent area flow channel, the reagent area includes a reagent area liquid storage portion and a droplet shape changing portion, the droplet shape changing portion is adjacent to the reagent area flow channel, and the reagent area liquid storage portion is on a side of the droplet shape changing portion away from the reagent area flow channel, and wherein the reagent area liquid storage portion, the droplet shape changing portion, and the reagent area flow channel are configured to generate an intermediate droplet from the reagent area liquid storage portion that covers the droplet shape changing portion and configured to change the shape of the intermediate droplet to generate a reagent droplet in the reagent area flow channel. This manufacturing method has advantages and effects similar to those described above with reference to the first substrate 102, and will not be repeated here.

In some embodiments, referring to FIGS. 2, 12, and 19, the first substrate further includes: a second electrode layer between the first base substrate and the first electrode layer; and an insulating layer between the first electrode layer and the second electrode layer, the second electrode layer includes a plurality of leads, a drive electrode in the first electrode layer and a lead corresponding to the drive electrode are connected by a via hole, and the via hole penetrates the insulating layer. For example, the method of manufacturing a first substrate for a microfluidic device may include: firstly preparing a second electrode layer 174 on the first base substrate optionally using a semiconductor process, and then fabricating an insulating layer 182, the first electrode layer 183, and an optional covering 176 on the second electrode layer 174, to form an intermediate product. In some embodiments, the formed intermediate product may be washed.

In some embodiments, referring to FIG. 2, FIG. 12, and FIG. 19, the first substrate further includes a first dielectric layer on a side of the first electrode layer away from the first base substrate, the method of manufacturing a first substrate for a microfluidic device may further include: preparing the first dielectric layer by atomic layer deposition. For example, after washing the above-mentioned intermediate product, the first dielectric layer 184 of polyimide is prepared by a high-temperature static pressure process or the first dielectric layer 184 is prepared by an atomic layer deposition process (such as an aluminum oxide layer, for the embodiments of specific process please refer to the description of FIGS. 20-22 below).

In some embodiments, referring to FIG. 2, FIG. 12, and FIG. 19, the first substrate may further include: a second dielectric layer between the first dielectric layer and the first lyophobic layer. For example, after the first dielectric layer 184 is fabricated as described above, the second dielectric layer 186 may be fabricated by an atomic layer deposition technique or a PECVD process.

In some embodiments, referring to FIG. 2, FIG. 12, and FIG. 19, the first substrate may further include: a first lyophobic layer on a side of the first dielectric layer away from the first base substrate. For example, after the second dielectric layer 186 is fabricated as described above, the first hydrophobic layer 188 is fabricated to form the first substrate.

In some embodiments, the microfluidic device includes a second substrate assembled with the first substrate, and the second substrate includes: a second base substrate; a conductive layer on the second base substrate; and a second lyophobic layer on a side of the conductive layer away from the second base substrate, where a space is defined between the first substrate and the second substrate. For example, a conductive layer and a second hydrophobic layer are fabricated on the second base substrate to form the second substrate. The formed first substrate and the formed second substrate are assembled to form a microfluidic device.

In some embodiments, after the covering 176 is formed and before the first dielectric layer 184 is formed, the formed intermediate product may be cut, and a blue film may be prepared through a screen printing process to protect the intermediate product and reduce the introduction of particles before the preparation of the next film layer.

Figure 20:
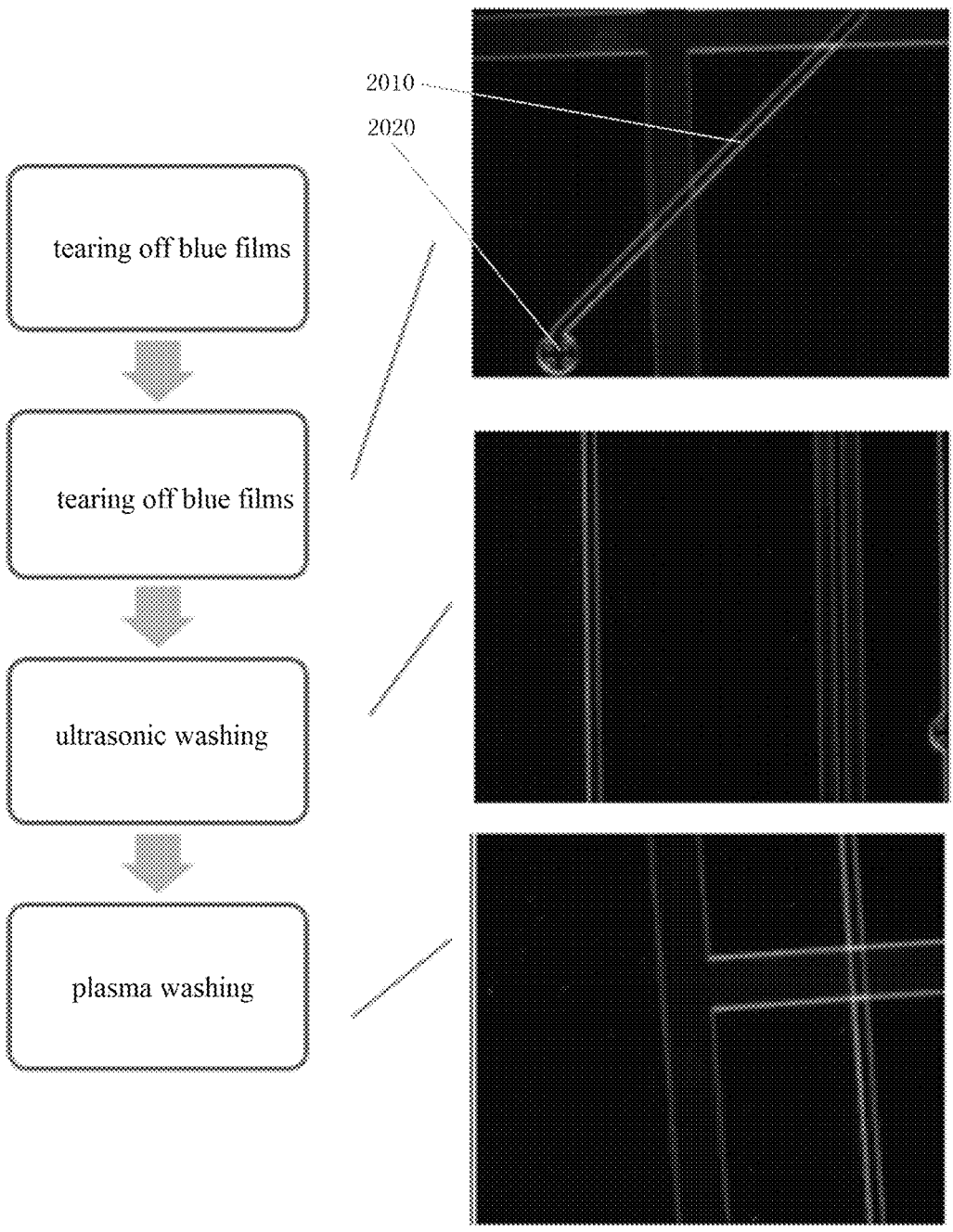
FIG. 20 shows a flowchart of the pretreatment process of preparing an aluminum oxide layer by atomic layer deposition, and the corresponding component surface, according to some embodiments of the present disclosure.

FIG. 20 shows a flow chart of the pretreatment process of preparing an aluminum oxide layer by atomic layer deposition and the corresponding component surface according to some embodiments of the present disclosure. In some embodiments, as shown in the flowchart of FIG. 20, before the preparation of the first dielectric layer 184, firstly the protective blue film on the surface of the component (i.e., the intermediate product formed by the previous process) needs to be torn off, and the component is left to stand for 2 days to remove static electricity. The surface of the component is observed under a dark field microscope to detect the size and quantity of particles (for example, at this time the surface of the component is shown in the first picture on the right in FIG. 20). After that, the components are ultrasonically washed, and the surface of the components is observed under a dark-field microscope to detect the size and quantity of particles (for example, at this time the surface of the component is shown in the second picture on the right in FIG. 20). Finally, perform plasma washing on the components (for example, using Ar gas), and observe the surface of the components under a dark-field microscope to detect the size and quantity of particles (for example, at this time the surface of the components is shown in the third picture on the right in FIG. 20). Wiring 2010, via holes 2020, and presence or absence of particles, etc. can be seen on the surface of the components.

After that, the first dielectric layer 184 (aluminum oxide) is prepared using atomic layer deposition technology, the precursors of which are $Al(CH_3)_3$ and $O_2$, and the reaction principle is:

$$2Al(CH_3)_3 + 6O_2 \rightarrow Al_2O_3 + 9H_2O$$

Figure 21:
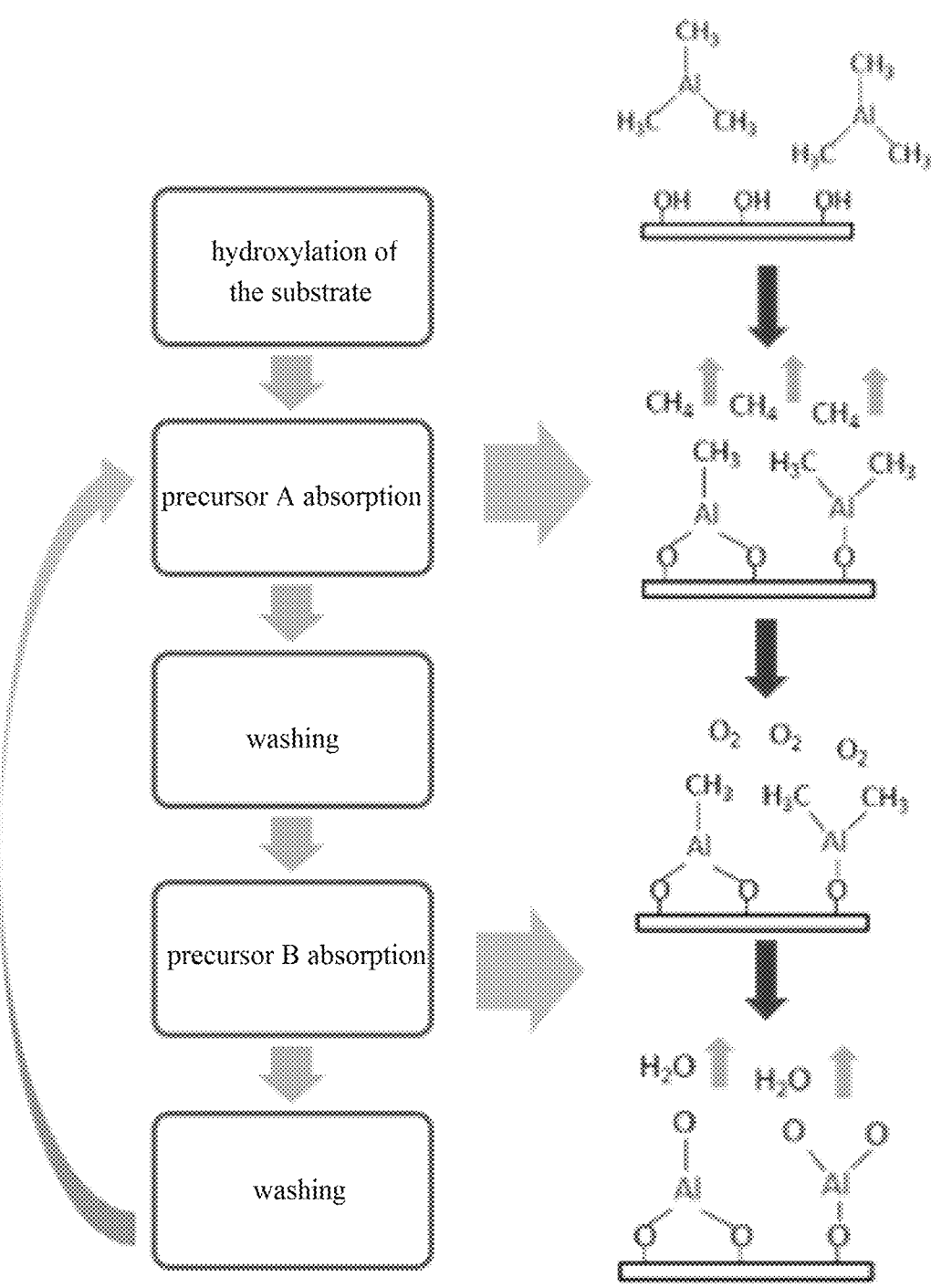
FIG. 21 schematically shows a flowchart of a film formation process of an aluminum oxide layer, and a corresponding principle diagram, according to some embodiments of the present disclosure.
Figure 22:
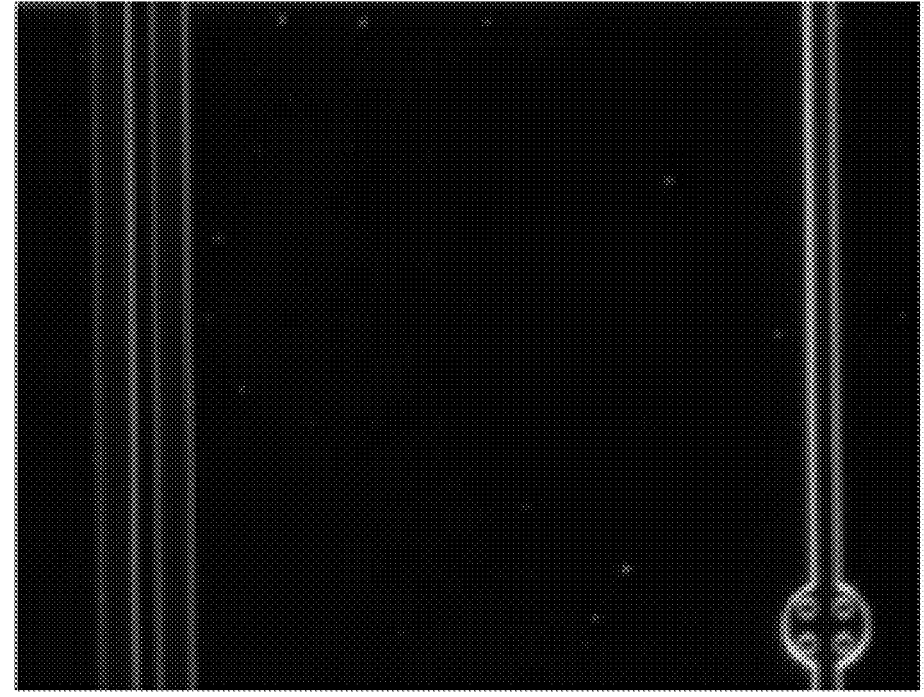
FIG. 22 shows the component surface after the aluminum oxide layer is prepared by atomic layer deposition, according to some embodiments of the present disclosure.

FIG. 21 schematically shows a flow chart of a film formation process of an aluminum oxide layer and a corresponding principle diagram according to some embodiments of the present disclosure. Firstly, the surface of the component is bombarded with plasma to achieve the hydroxylation of the substrate, and then the precursor A $Al(CH_3)_3$ is introduced to make the Al atoms adsorb on the surface of the substrate and release the by-product ($CH_4$), and then the protective gas ($N_2$) is introduced to wash the chamber to ensure that the excess precursor A and by-products are discharged from the chamber. After that, the precursor B ($O_2$) is introduced to make it adsorb with Al atoms and release the by-products, and then the protective gas $N_2$ is introduced to wash the chamber to ensure that the excess precursor B and by-products are discharged from the chamber. Repeat this process until the aluminum oxide layer reaches the desired thickness (for example, 300 nm). FIG. 22 shows the surface of the component after the aluminum oxide layer is prepared by atomic layer deposition according to some embodiments of the present disclosure. After completing the preparation of this layer, the surface of the component is observed under a dark-field microscope to detect the size and quantity of particles. The preparation method of the aluminum oxide layer realized by the atomic layer deposition technology has advantages and effects similar to those described above with respect to the first substrate 102, which will not be repeated here. After testing, when the second dielectric layer is not used but only the first dielectric layer 184 (prepared by the method shown in FIGS. 20-22) is used, the microfluidic device made by such a first substrate 102 can drive 17 kinds of library construction reagents and 9 kinds of conventional reagents without dielectric layer breakdown at 95° C. with the driving voltage of 20 Vrms. The driving voltage of some alcohol reagents such as methanol, ethanol, isopropanol, etc. can be reduced to no more than 10 Vrms.

As will be apparent to those skilled in the art, many different ways of performing the methods of these embodiments of the present disclosure are possible. For example, the order of the steps can be changed, or some steps can be executed in parallel. In addition, other method steps can be inserted between the steps. The inserted step may represent an improvement of the method such as described herein, or may be unrelated to the method. In addition, a given step may not be fully completed before the next step starts. It should be understood that, without contradicting each other, the features of different embodiments in the present disclosure can be used in combination with each other.

Those skilled in the art can make various changes and modifications to the present disclosure without departing from the spirit and scope of the present disclosure. In this way, if these modifications and variations of the present disclosure fall within the scope of the claims of the present disclosure and their equivalent technologies, the present disclosure is also intended to include these modifications and variations.

The invention claimed is:

1. A first substrate for a microfluidic device, comprising:

a first base substrate;

a first electrode layer on the first base substrate, the first electrode layer comprising a plurality of drive electrodes;

a first dielectric layer on a side of the first electrode layer away from the first base substrate;

a first lyophobic layer on a side of the first dielectric layer away from the first base substrate; and a second dielectric layer between the first dielectric layer and the first lyophobic layer;

wherein the first lyophobic layer is patterned with periodically arranged openings, so that the second dielectric layer is periodically exposed by the openings, and a material of the second dielectric layer comprises silicon oxide.

2. The first substrate according to claim 1, wherein the plurality of drive electrodes comprise at least one flow channel and at least one functional area in the first substrate, the at least one functional area comprises a reagent area, the at least one flow channel comprises a reagent area flow channel, the reagent area comprises a reagent area liquid storage portion and a droplet shape changing portion, the droplet shape changing portion is adjacent to the reagent area flow channel, and the reagent area liquid storage portion is on a side of the droplet shape changing portion away from the reagent area flow channel, wherein the droplet shape changing portion comprises:

a first electrode module comprising one or more electrodes, the first electrode module being arranged in a shape with a notch; and a second electrode module, the second electrode module being embedded in the notch, and wherein a sum of a projected area of the first electrode module on the first base substrate and a projected area of the second electrode module on the first base substrate is smaller than a projected area of the reagent area liquid storage portion on the first base substrate, and the reagent area flow channel comprises a drive electrode, and the second electrode module is adjacent to the drive electrode of the reagent area flow channel.

3. The first substrate according to claim 2, wherein reagent area flow channel comprises a central axis, and the first electrode module is arranged in a symmetrical shape with respect to the central axis.

4. The first substrate according to claim 2, wherein an overall shape of a drive electrode comprised in the droplet shape changing portion is a rectangle with two sides perpendicular to an extension direction of the reagent area flow channel, and two corners of the rectangle on a side adjacent to the reagent area flow channel are provided with chamfers.

5. The first substrate according to claim 2, wherein the first electrode module comprises a fourth electrode, a sixth electrode, and a seventh electrode, and the second electrode module comprises a fifth electrode, the reagent area liquid storage portion comprises a first electrode, a second electrode, and a third electrode sequentially arranged along an extension direction of the reagent area flow channel;

the droplet shape changing portion comprises the fourth electrode and the fifth electrode sequentially arranged along the extension direction of the reagent area flow channel on a side of the third electrode away from the first electrode, and the sixth electrode and the seventh electrode on both sides of the fourth electrode and the fifth electrode perpendicular to the extension direction of the reagent area flow channel; and the reagent area flow channel comprises an eighth electrode and a ninth electrode sequentially arranged along the extending direction of the reagent area flow channel on a side of the fifth electrode away from the first electrode.

6. The first substrate according to claim 5, wherein the shape of the first electrode is a rectangle, two parallel sides of the rectangle are perpendicular to the extension direction of the reagent area flow channel, and the rectangle is provided with chamfers at two corners, and the two corners are away from the second electrode in a direction parallel to the extension direction of the reagent area flow channel.

7. The first substrate according to claim 2, wherein the at least one functional area further comprises a waste liquid area, and the at least one flow channel further comprises a waste liquid area flow channel, the waste liquid area comprises a waste liquid area liquid storage portion and a waste liquid area transition portion, the waste liquid area transition portion is adjacent to the waste liquid area flow channel, and the waste liquid area liquid storage portion is on a side of the waste liquid area transition portion away from the waste liquid area flow channel, a drive electrode comprised in the waste liquid area transition portion is in a long strip shape, long sides of the long strip shape are perpendicular to an extension direction of the waste liquid area flow channel, among drive electrodes comprised in the waste liquid area liquid storage portion a drive electrode adjacent to the waste liquid area transition portion comprises a notch, and the drive electrode comprised in the waste liquid area transition portion is embedded in the notch.

8. The first substrate according to claim 7, wherein the drive electrode comprised in the waste liquid area is provided with chamfers at positions corresponding to corners of the waste liquid area.

9. The first substrate according to claim 2, wherein the at least one functional area further comprises a sample inlet area, and the at least one flow channel further comprises a sample inlet area flow channel, the sample inlet area comprises a sample inlet area liquid storage portion and a sample inlet area transition portion, the sample inlet area transition portion is adjacent to the sample inlet area flow channel, and the sample inlet area liquid storage portion is on a side of the sample inlet area transition portion away from the sample inlet area flow channel, among drive electrodes comprised in the sample inlet area liquid storage portion a drive electrode adjacent to the sample inlet area transition portion comprises a notch, and a drive electrode comprised in the sample inlet area transition portion is embedded in the notch.

10. The first substrate according to claim 9, wherein an overall shape of a drive electrode comprised in the sample inlet area is a rectangle with two sides perpendicular to an extension direction of the sample inlet area flow channel, and two corners of the rectangle on a side adjacent to the sample inlet area flow channel are provided with chamfers.

11. The first substrate according to claim 2, wherein the at least one functional area further comprises a temperature control area, a sampling area and a quality detection area, and the at least one flow channel further comprises a temperature control area flow channel, a sampling area flow channel and a quality detection area flow channel.

12. The first substrate according to claim 11, wherein the first substrate has a rectangular shape, a direction parallel to two long sides of the rectangular shape is a first direction, and the first substrate comprises at least one column of temperature control branch, each column of the at least one column of temperature control branch extends along the first direction and comprises:

the reagent area, the sampling area, the temperature control area, a sample inlet area and a waste liquid area sequentially arranged along the first direction.

13. The first substrate according to claim 11, wherein the temperature control area comprises an opening in the first electrode layer and between the drive electrodes, the temperature control area further comprises a temperature sensor, and the temperature sensor is provided in the opening.

14. The first substrate of claim 13, wherein a material of the drive electrodes and the temperature sensor comprises molybdenum.

15. The first substrate according to claim 1, further comprising:

coverings on the drive electrodes, wherein the coverings cover surfaces of the drive electrodes excluding a surface opposite to the first base substrate, and a material of the coverings comprises ITO.

16. The first substrate according to claim 13, further comprising:

a covering on the temperature sensor, wherein the covering covers surfaces of the temperature sensor excluding a surface opposite to the first base substrate, and a material of the covering comprises ITO.

17. The first substrate according to claim 1, further comprising:

a second electrode layer between the first base substrate and the first electrode layer; and an insulating layer between the first electrode layer and the second electrode layer, wherein, the second electrode layer comprises a plurality of leads, a drive electrode in the first electrode layer and a lead corresponding to the drive electrode are connected by a via hole, and the via hole penetrates the insulating layer.

18. The first substrate according to claim 1, wherein a material of the first dielectric layer comprises aluminum oxide or polyimide.

19. The first substrate according to claim 1, wherein the first base substrate comprises glass.

20. A microfluidic device, comprising:

the first substrate according to claim 1; and a second substrate assembled with the first substrate, the second substrate comprising:

a second base substrate;

a conductive layer on the second base substrate; and a second lyophobic layer on a side of the conductive layer away from the second base substrate, wherein, a space is defined between the first substrate and the second substrate.

21. The microfluidic device according to claim 20, wherein a ground electrode is provided on periphery of the first substrate, and the conductive layer of the second substrate is electrically connected to the ground electrode.

* * * * *